(12) United States Patent
Rossi

(10) Patent No.: US 7,070,996 B2
(45) Date of Patent: Jul. 4, 2006

(54) PRODUCTION OF CULTURED HUMAN MAST CELLS AND BASOPHILS FOR HIGH THROUGHPUT SMALL MOLECULE DRUG DISCOVERY

(75) Inventor: Alexander B. Rossi, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/053,355

(22) Filed: Nov. 8, 2001

(65) Prior Publication Data

US 2003/0077824 A1     Apr. 24, 2003

Related U.S. Application Data

(60) Provisional application No. 60/316,723, filed on Aug. 31, 2001.

(51) Int. Cl.
*C12N 5/02* (2006.01)
*C12N 5/10* (2006.01)
*C12N 5/08* (2006.01)

(52) U.S. Cl. ..................... 435/377; 435/325; 435/355; 435/363; 435/372; 435/375; 424/93.1

(58) Field of Classification Search ............... 435/325, 435/375, 6
See application file for complete search history.

(56) References Cited

U.S. PATENT DOCUMENTS

| | | | |
|---|---|---|---|
| 4,559,310 A | 12/1985 | Cantor et al. |
| 5,554,512 A | 9/1996 | Lyman et al. |
| 5,843,423 A | 12/1998 | Lyman et al. |
| 6,190,655 B1 | 2/2001 | Lyman et al. |
| 6,225,044 B1 | 5/2001 | Klein et al. |
| 6,261,841 B1 | 7/2001 | Cohen et al. |

OTHER PUBLICATIONS

Ahn et al, J Allergy Cin Immunol 2000;106:321-8.*
Kinoshita et al, Blood 1999;94:496-508.*
Matsushima et al, J Dermatol Sci 2000;24:4-13.*
Demo et al, Cytometry 1999;36:340-8.*
Janaki et al, J Ethonopharmacol 1999;67:45-51.*
Schwinger et al, Ann Hematol 1999;78:364-70.*
Qui et al, J Hematother Stem Cell Res 1999;8:609-18.*
Saito, H., et al., "Characterization of cord-blood-derived human mast cells cultured in the presence of Steel factor and interleukin-6," *Int Arch Allergy Immunol.* May-Jun. 1995; 107(1-3):63-5.
Saito, H., et al., "Selective growth of human mast cells induced by Steel factor, IL-6, and prostaglandin E2 from cord blood mononuclear cells," *J Immunol.* Jul. 1, 1996;157(1):343-50.
Suzuki, H., et al., "Early and late events in Fc epsilon RI signal transduction in human cultured mast cells," *J Immunol.* Dec. 15, 1997;159(12):5881-8.
Toru, H., et al., "Induction of the high-affinity IgE receptor (Fc epsilon RI) on human mast cells by IL-4," *Int Immunol.* Sep. 8, 1996;(9):1367-73.
Valent, P. and Bettelheim, P., "Cell surface structures on human basophils and mast cells: biochemical and functional characterization," *Adv Immunol.* 1992;52:333-423.
Wognum, A.W., et al., "Stimulation of mouse bone marrow cells with kit ligand, FLT3 ligand, and thrombopoietin leads to efficient retrovirus-mediated gene transfer to stem cells, whereas interleukin 3 and interleukin 11 reduce transduction of short- and long-term repopulating cells," *Hum Gene Ther.* Oct. 10, 2000;11(15):2129-41.
Yamaguchi, M., et al., "IgE enhances Fc epsilon receptor I expression and IgE-dependent release of histamine and lipid mediators from human umbilical cord blood-derived mast cells: synergistic effect of IL-4 and IgE on human mast cell Fc epsilon receptor I expression and mediator release," *J Immunol.* May 1, 1999;162(9):5455-65.

(Continued)

*Primary Examiner*—Q. Janice Li
(74) *Attorney, Agent, or Firm*—Dechert LLP

(57) ABSTRACT

Provided are methods for producing and screening proliferated populations of CD34-negative progenitor cells, mucosal mast cells, connective tissue-type mast cells and basophil cells. The methods generate uniform proliferated populations of cells. The proliferated populations contain a uniform population of a size suitable for use in high throughput screening methods, for example, screening for agents that alter exocytosis. The invention includes screening the proliferated populations with at least one candidate bioactive agent, and evaluating the cells to detect a cell with an altered phenotype. The invention also includes isolating a candidate bioactive agent that causes the altered phenotype. Additionally, cells formed according to the described methods are also encompassed by the invention.

14 Claims, 14 Drawing Sheets

OTHER PUBLICATIONS

Yanagida, M., et al., "Effects of T-helper 2-type cytokines, interleukin-3 (IL-3), IL-4, IL-5, and IL-6 on the survival of cultured human mast cells," *Blood.* Nov. 15, 1995;86(10):3705-14.

Zhang, X, et al., "Influence of FL on ex vivo expansion of hematopoietic cells from cord blood in long-term liquid cultures," *Chin J Biotechnol.* 1999;15(3):189-94.

Bingham, C.O. 3rd and Austen, KF., "Mast-cell responses in the development of asthma," *J Allergy Clin Immunol.* Feb. 2000;105(2 Pt 2):S527-34.

Bischoff, S.C., et al., "Functional properties of human intestinal mast cells cultured in a new culture system: enhancement of IgE receptor-dependent mediator release and response to stem cell factor," *J Immunol.* Dec. 1, 1997;159(11):5560-7.

Denburg, J.A., "Basophil and mast cell lineages in vitro and in vivo," *Blood.* Feb. 15, 1992;79(4):846-60.

Dvorak, A.M., "New aspects of mast cell biology," *Int Arch Allergy Immunol.* Sep. 1997;114(1):1-9.

Ghannadan, M., et al., "Phenotypic characterization of human skin mast cells by combined staining with toluidine blue and CD antibodies," *J Invest Dermatol.* Oct. 1998;111(4):689-95.

Gilmore, G.L., et al., "Ex vivo expansion of human unbilical cord blood and peripheral blood CD34(+) hematopoietic stem cells," *Exp Hematol.* Nov. 28, 2000;(11):1297-305.

Gordon, J.R., et al., "Mast cells as a source of multifunctional cytokines," *Immunol Today.* Dec. 11, 1990;(12):458-64.

Hacein-Bey, S., et al., "Optimization of retroviral gene transfer protocol to maintain the lymphoid potential of progenitor cells," *Hum Gene Ther.* Feb. 10, 2001;12(3):291-301.

Ishizaka, T. et al., "Development of human mast cells from their progenitors." *Curr Opin Immunol.* Dec. 5, 1993;(6):937-43.

Kempuraj, D., et al., "Characterization of mast cell-committed progenitors present in human umbilical cord blood," *Blood.* May 15, 1999;93(10):3338-46.

Kinoshita, T., et al., "Interleukin-6 directly modulates stem cell factor-dependent development of human mast cells derived from CD34(+) cord blood cells," *Blood.* Jul. 15, 1999;94(2):496-508.

Kirshenbaum, A.S., et al., "Demonstration that human mast cells arise from a progenitor cell population that is CD34(+), c-kit(+), and expresses aminopeptidase N (CD13)," *Blood.* Oct. 1, 1999;94(7):2333-42.

Lazzari, L., et al., "Comparison of different serum-free media for ex vivo expansion of HPCs from cord blood using thrombopoietin, Flt-3 ligand, IL-6, and IL-11," *Transfusion.* May 2001;41(5):718-9.

Nakahata, et al., "Synergy of stem cell factor and other cytokines in mast cell development," in *Biological and Molecular Aspects of Mast Cell and Basophil Differentiation and Function*, Kitamura et al. (eds.) Raven Press, Ltd.: New York, 1995, pp. 13-24.

Otto, K.G., et al., "Cell proliferation through forced engagement of c-Kit and Flt-3," *Blood.* Jun. 1, 2001;97(11):3662-4.

Rappold, I. et al., "Functional and phenotypic characterization of cord blood and bone marrow subsets expressing FLT3 (CD135) receptor tyrosine kinase," *Blood.* Jul. 1, 1997;90(1):111-25.

Robinson, S., et al., "Comparison of the hematopoietic activity of flt-3 ligand and granulocyte-macrophage colony-stimulating factor acting alone or in combination," *J Hematother Stem Cell Res.* Oct. 9, 2000;(5):711-20.

McKenna, H.J., et al., "Effect of flt3 Ligand on the Ex Vivo Expansion of Human $CD34^{+}$ Hematopoietic Progenitor Cells", *Blood* 86 (9):3413-3420 (1995).

Siitonen, T. et al., "Flt-3 ligand does not induce the growth of peripheral blood granulocyte-macrophage colony-forming cells in myeloproliferative disorders", *European Journal of Haematology* 62:103-108 (1999).

Shichijo et al., "The effects of anti-asthma drugs on mediator release from cultured human mast cells," *Clinical and Experimental Allergy* 28(10):1228-1236 (1998).

Rossi et al., "Development and utilization of cultured human mast cells for high throughput small molecule drug discovery," *Molecular Biology of the Cell* 12:512A-513A (2001).

Igarishi et al., "Characteristics of histamine release from cultured human mast cells", *Clinical and Experimental Allergy* 26(5):597-602 (1996).

Hoffman et al., "Determination of the allergenic activity of birch pollen and apple prick test solutions by measurement of beta-hexosaminidase release from RBL-2H3 cells. Comparison with classical methods in allergen standardization," *Allergy* 54(5):446-454 (1999).

Ikawati et al., "Screening of several Indonesian medicinal plants for their inhibitory effect on histamine release from RBL-2H3 cells," *Journal of Ethnopharmacology* 75(2-3):249-256 (2001).

Okayama, Y., "Human Cultured Mast Cells", Clinical and Experimental Allergy, Aug. 2000, 30(8):1053-1055.

Rottem, M., et al., "Mast Cells Cultured form the Peripheral Blood of Normal Donors and Patients with Mastocytosis Originate for a CD34+/Fc-$\epsilon$-RI$^{*}$ cell population", Blood, 1994, 84(8):2489-2496.

* cited by examiner

SEQ ID NO:1

MTQDCSFQHS PISSDFAVKI RELSDYLLQD YPVTVASNLQ
DEELCGGLWR LVLAQRWMER LKTVAGSKMQ HFVTKCAFQP
PPSCLRFVQT NISRLLQETS EQLVALKPWI TRQNFSRCLE
LQCQPDSSTL PPPWSPRPLE ATAPTA

FIG._1

SEQ ID NO:2

MEGICRNRVT NNVKDVTKLV ANLPKDYMIT LKYVPGMDVL
PSHCWISEMV VQLSDSLTDL LDKFSNISEG LSNYSIIDKL
VNIVDDLVEC VKENSSKDLK KSFKSPEPRL FTPEEFFRIF
NRSIDAFKDF VVASETSDCV VSSTLSPEKD SRVSVTKPFM
LPPVA

FIG._2

SEQ ID NO:3

PVPPGEDSKD VAAPHRQPLT SSERIDKQIR YILDGISALR
KETCNKSNMC ESSKEALAEN NLNLPKMAEK DGCFQSGFNE
ETCLVKIITG LLEFEVYLEY LQNRFESSEE QARAVQMSTK
VLIQFLQKKA KNLDAITTPD PTTNASLLTK LQAQNQWLQD
MTTHLILRSF KEFLQSSLRA LRQM

FIG._3

SEQ ID NO:4

MHKCDITLQE IIKTLNSLTE QKTLCTELTV TDIFAASKNT
TEKETFCRAA TVLRQFYSHH EKDTRCLGAT AQQFHRHKQL
IRFLKRLDRN LWGLAGLNSC PVKEANQSTL ENFLERLKTI
MREKYSKCSS

FIG._4

SEQ ID NO:5

MAPMTQTTSL KTSWVNCSNM IDEIITHLKQ PPLPLLDFNN
LNGEDQDILM ENNLRRPNLE AFNRAVKSLQ NASAIESILK
NLLPCLPLAT AAPTRHPIHI KDGDWNEFRR KLTFYLKTLE
NAQAQQTTLS LAIF

FIG._5

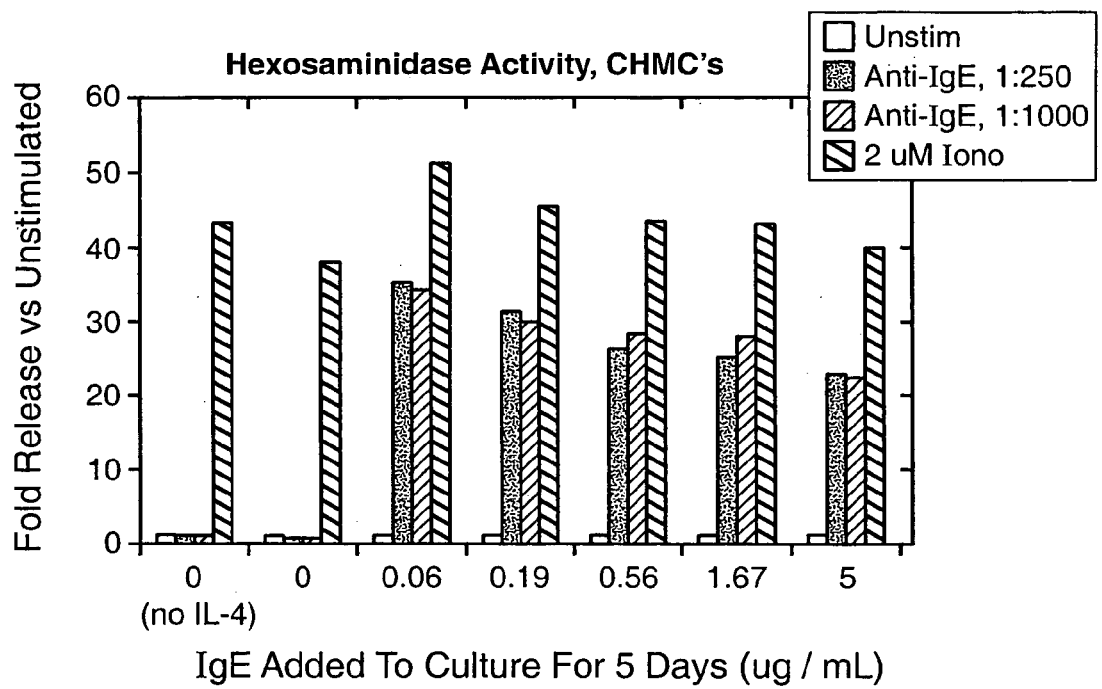
FIG._6A
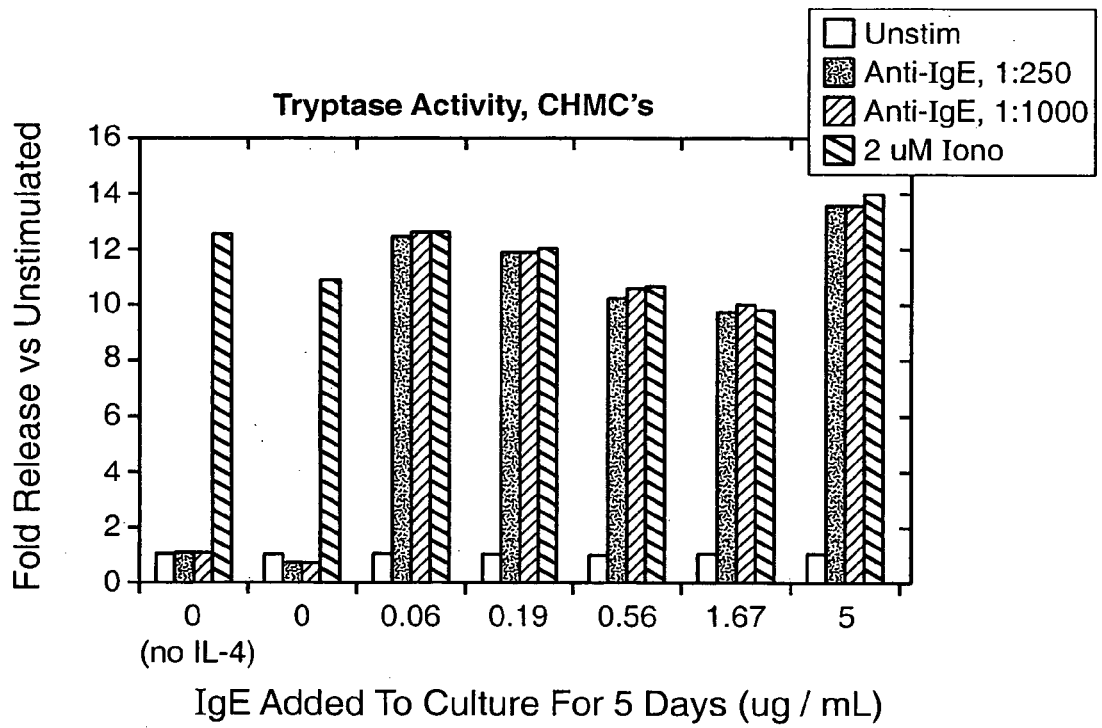
FIG._6B

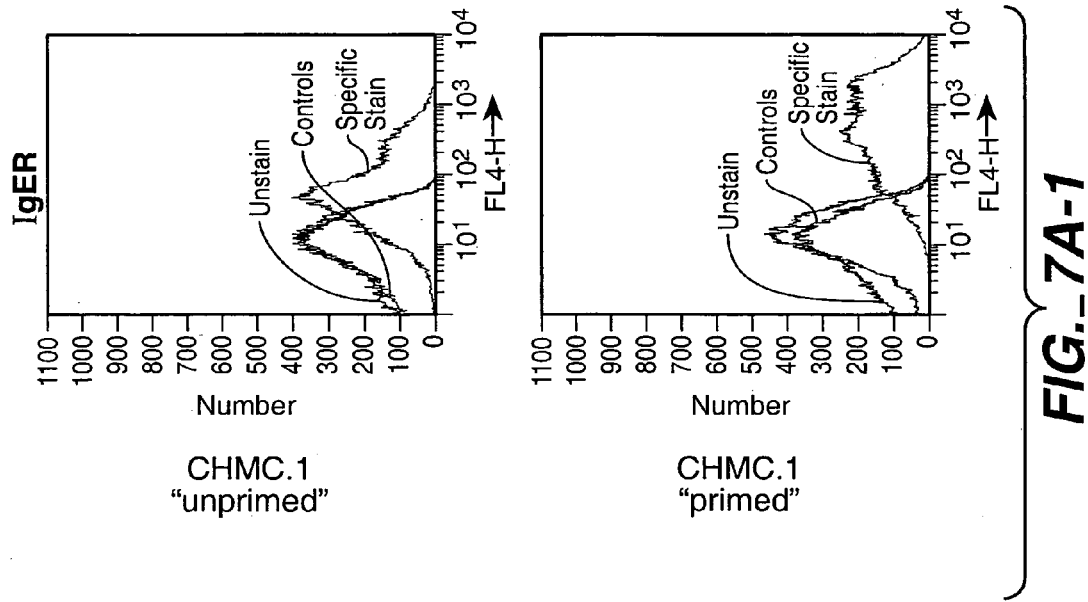

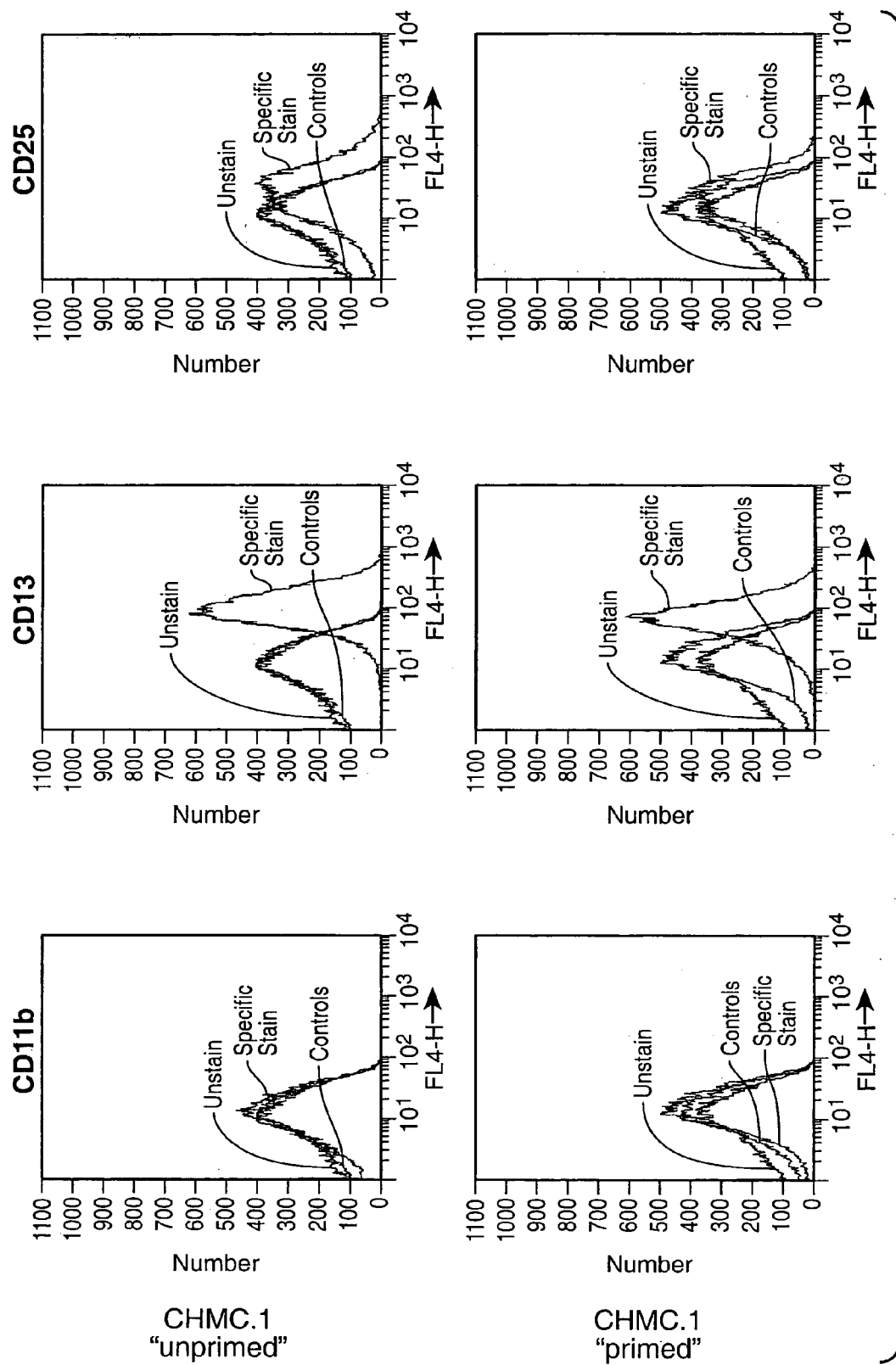
FIG._7A-2

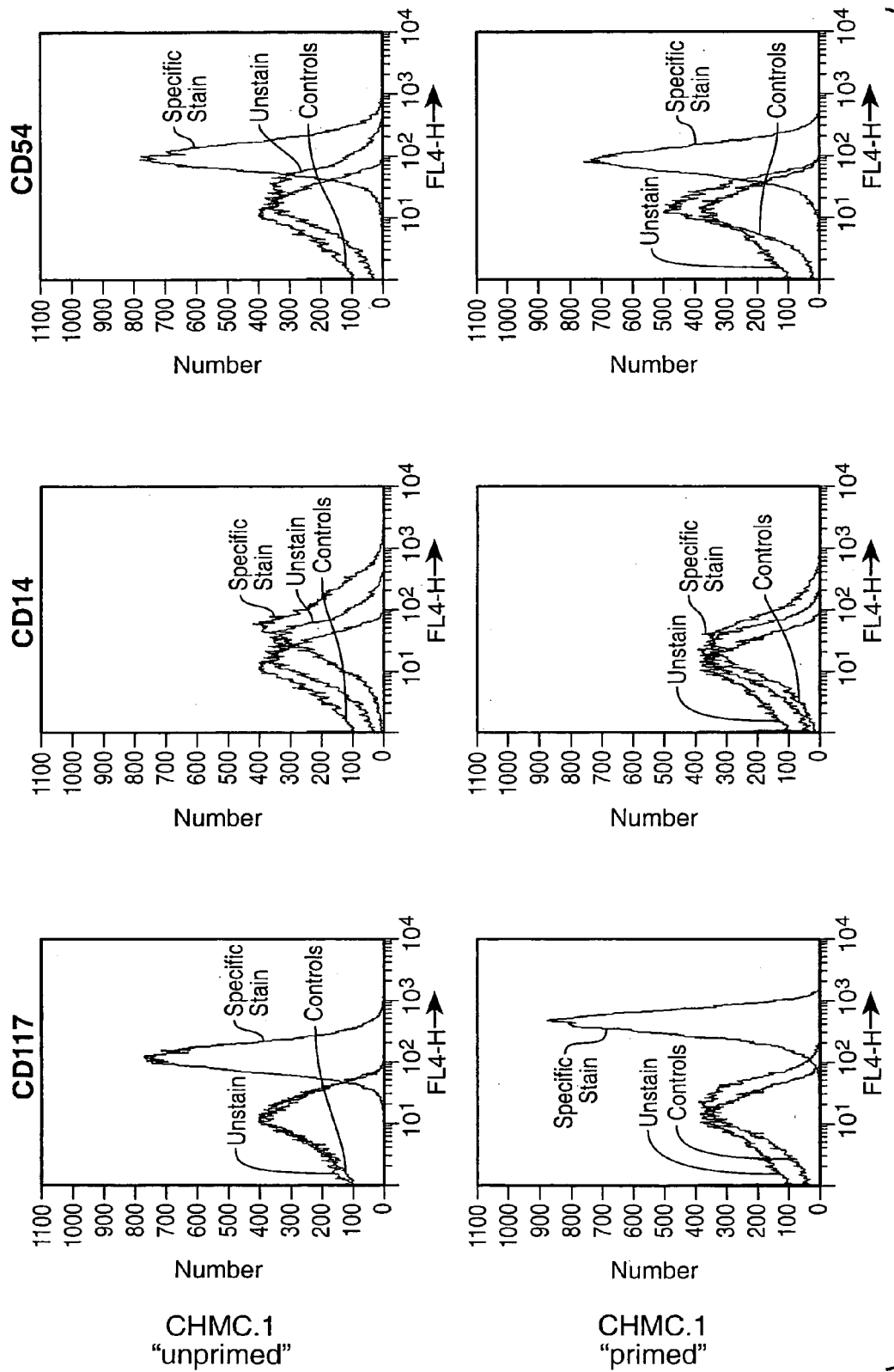
FIG._7A-3

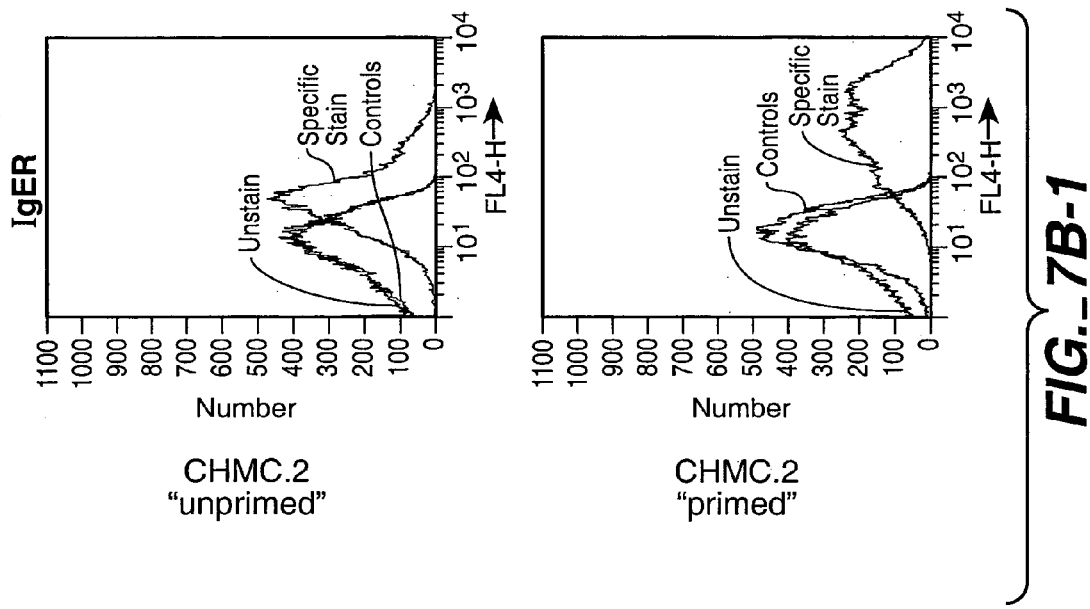

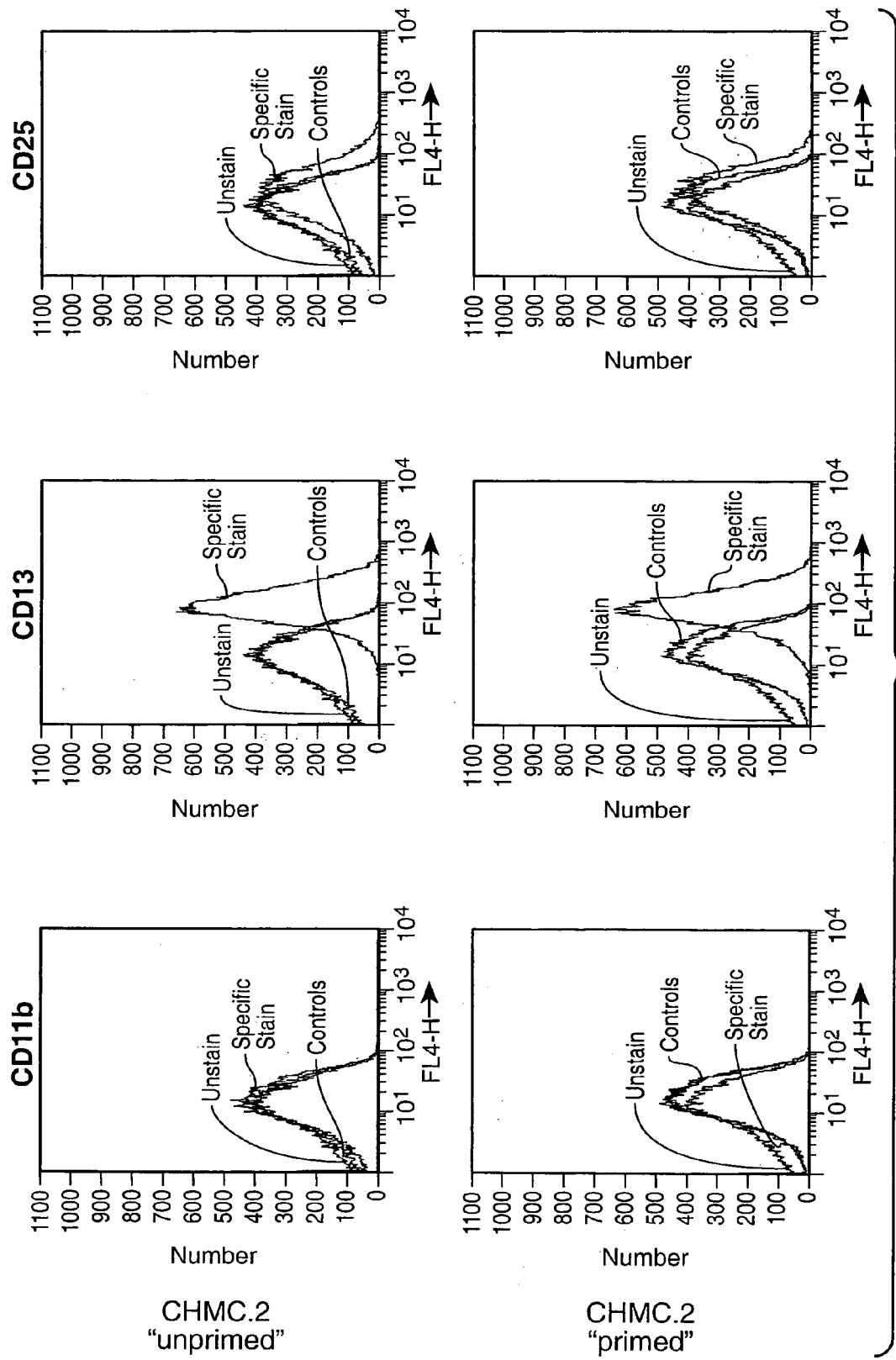
FIG._7B-2

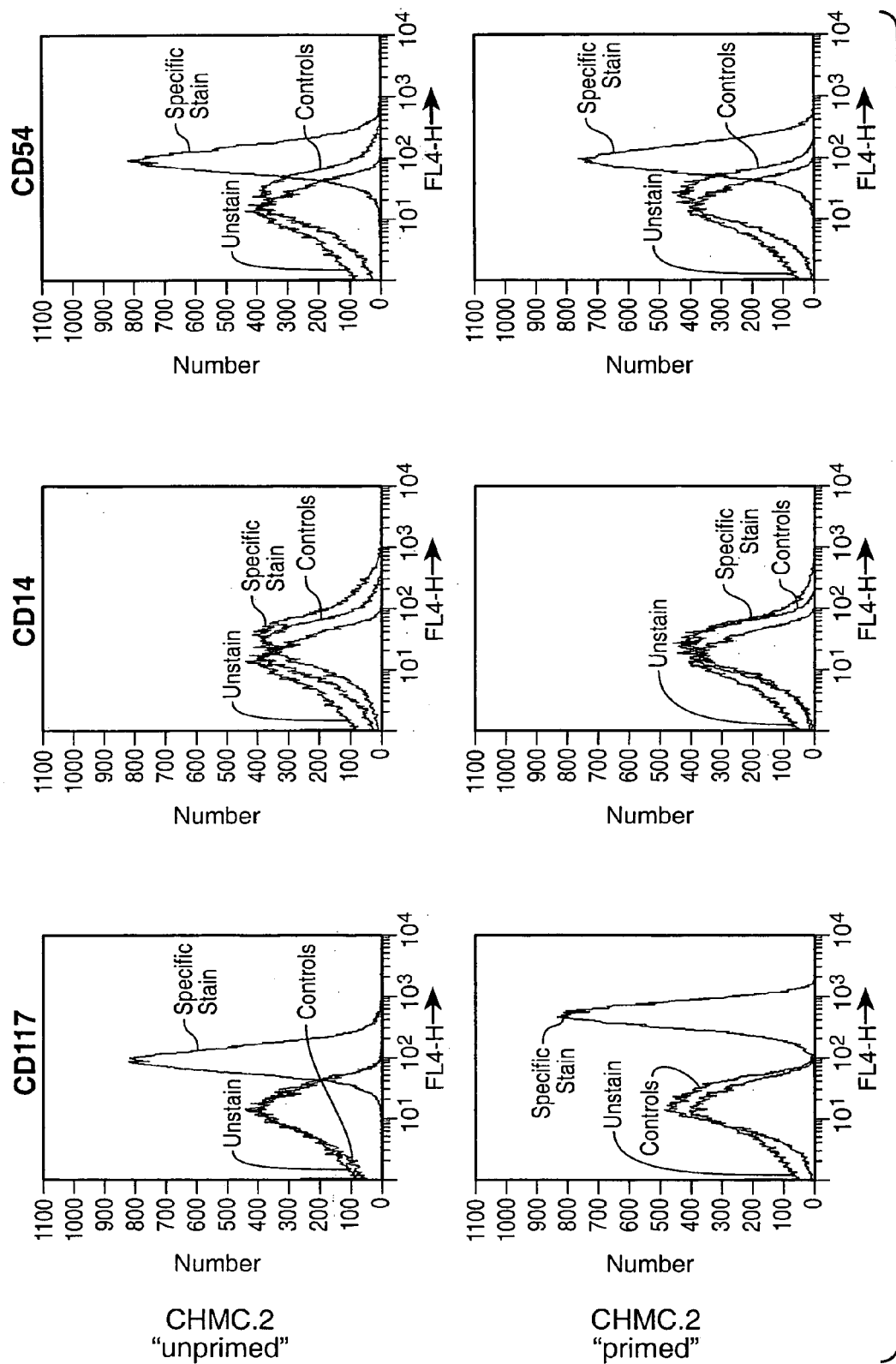
FIG._7B-3

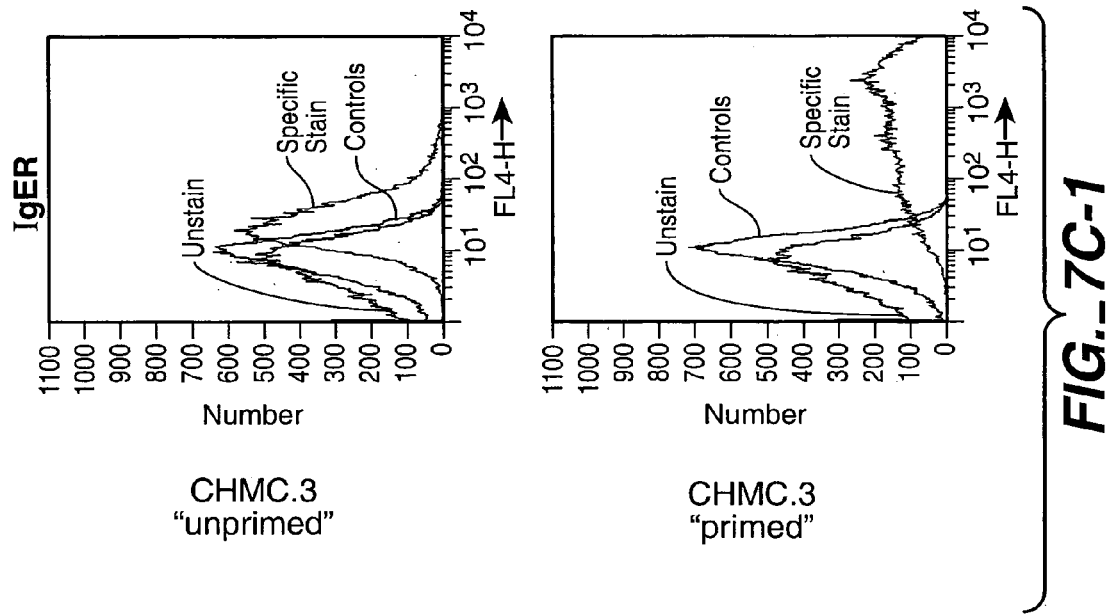

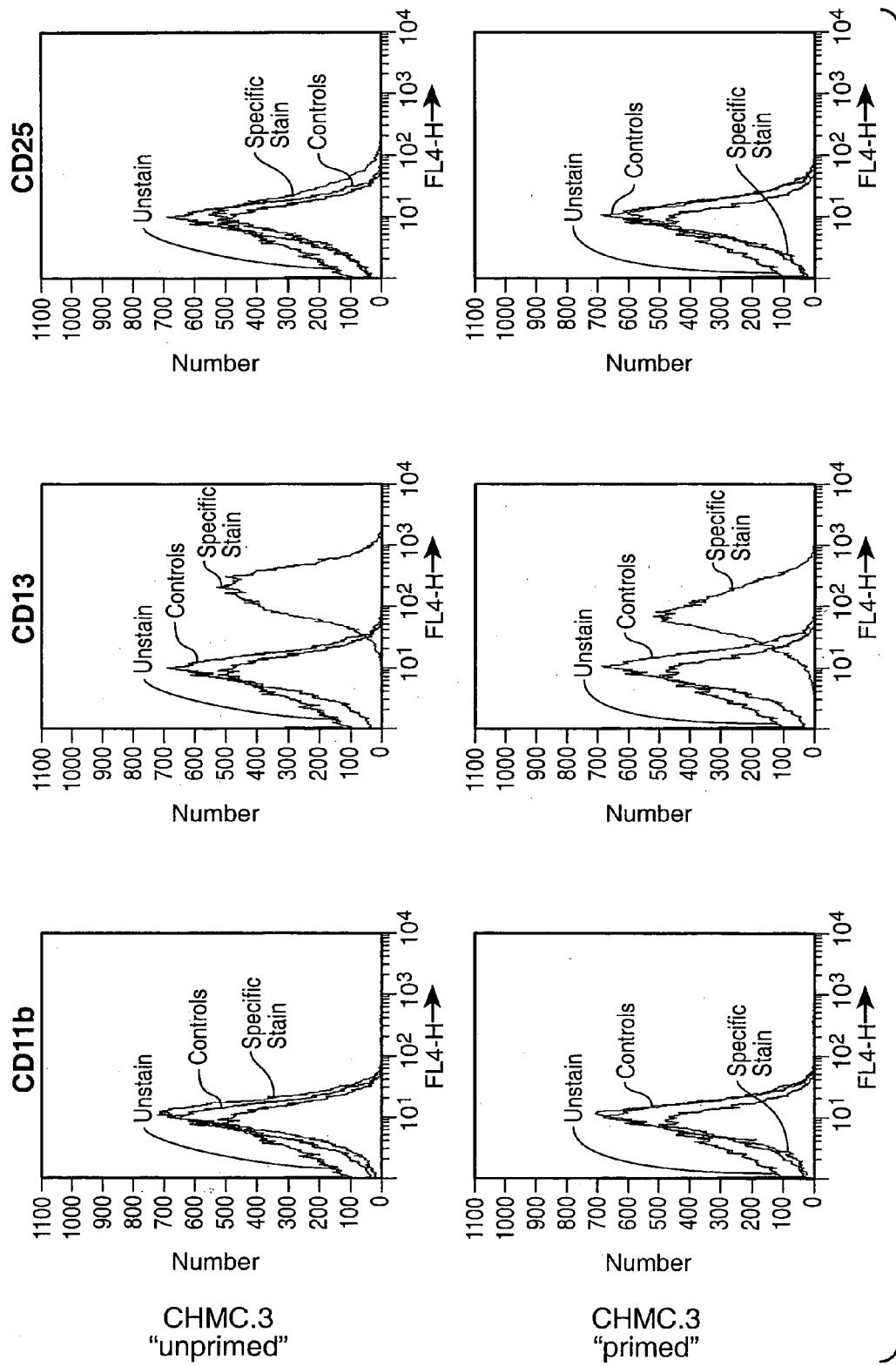

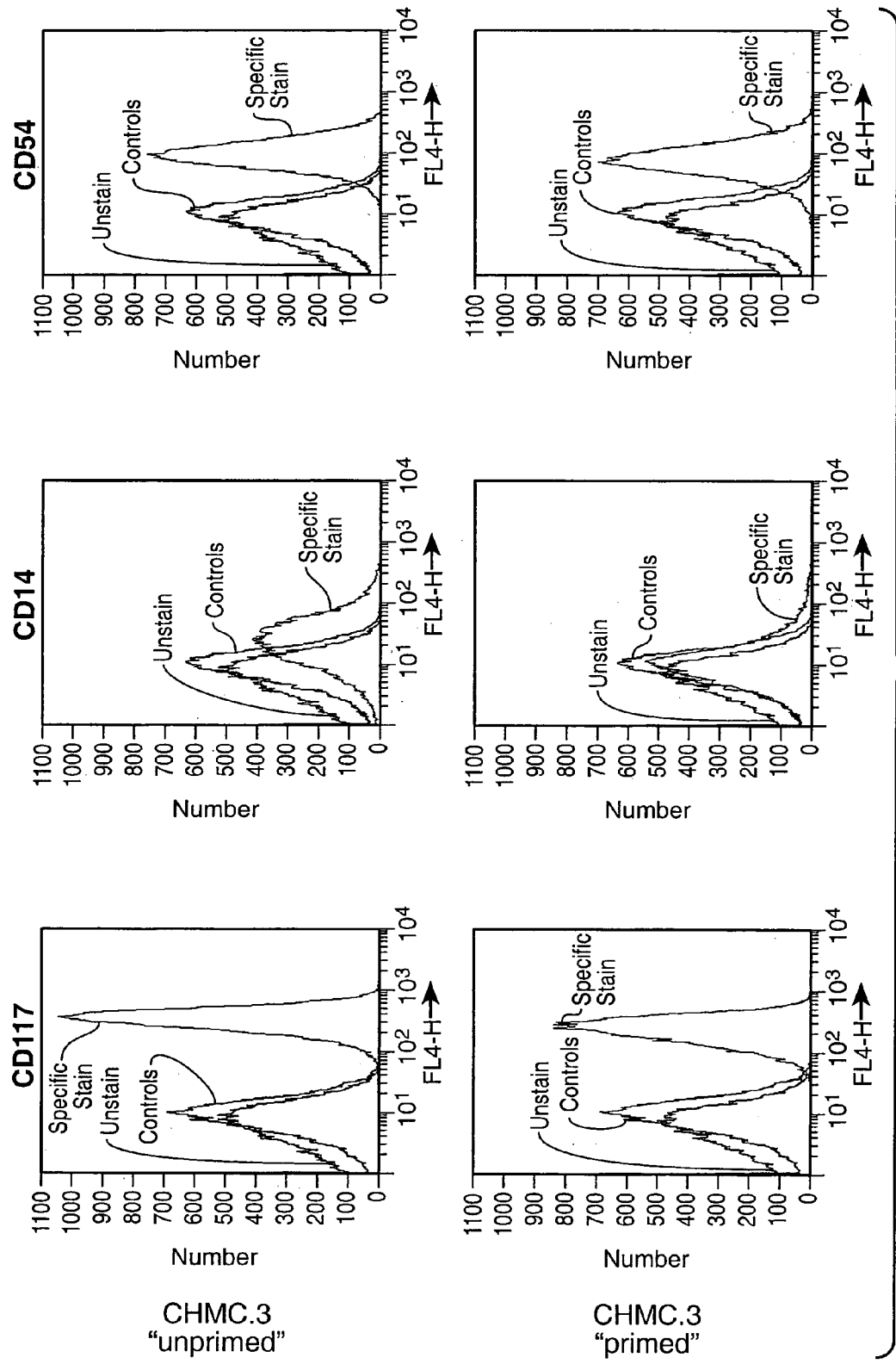
FIG._7C-3

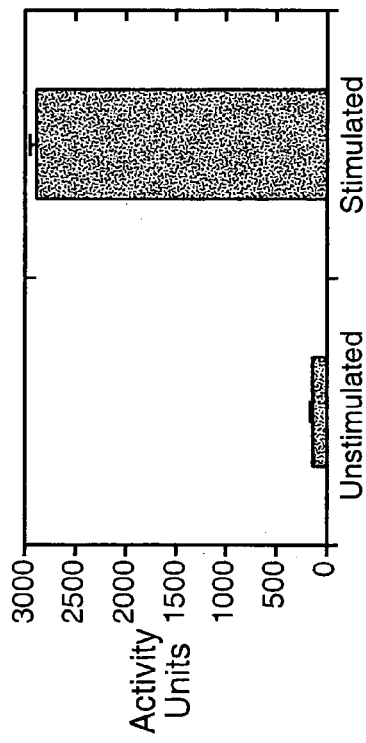
FIG._8A
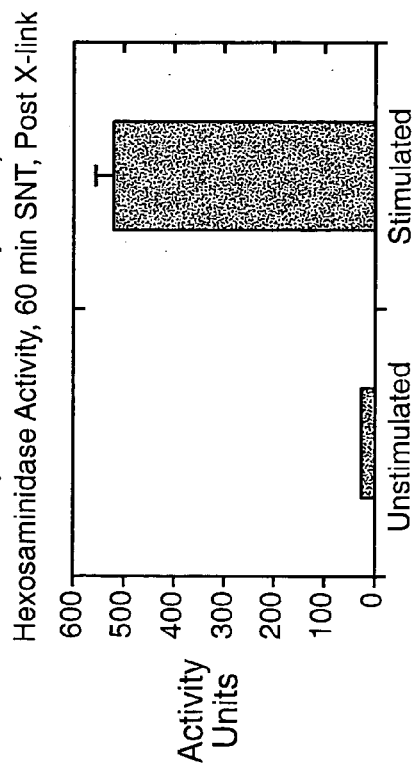
FIG._8C
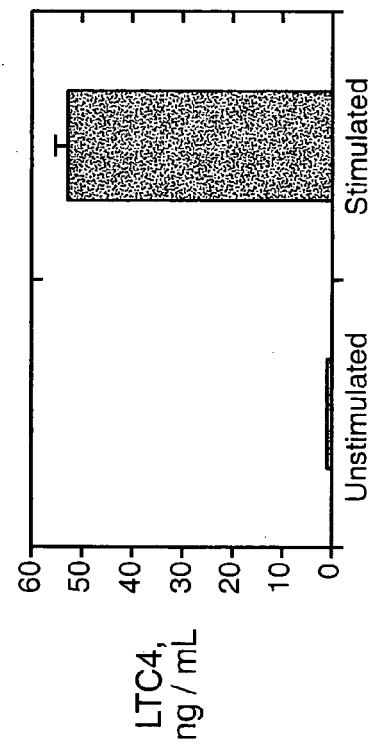
FIG._8B
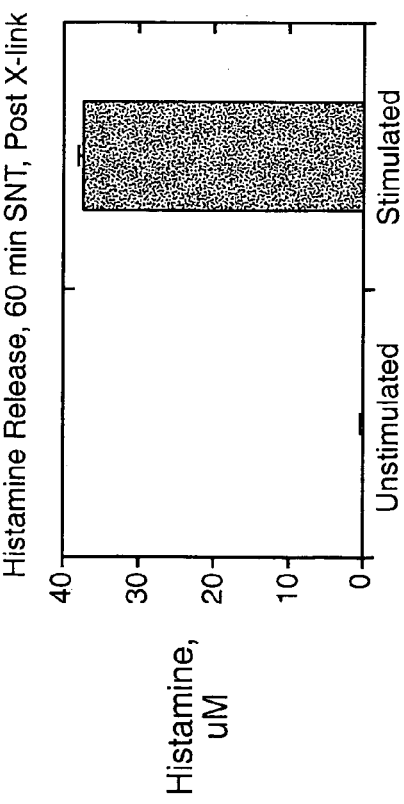
FIG._8D

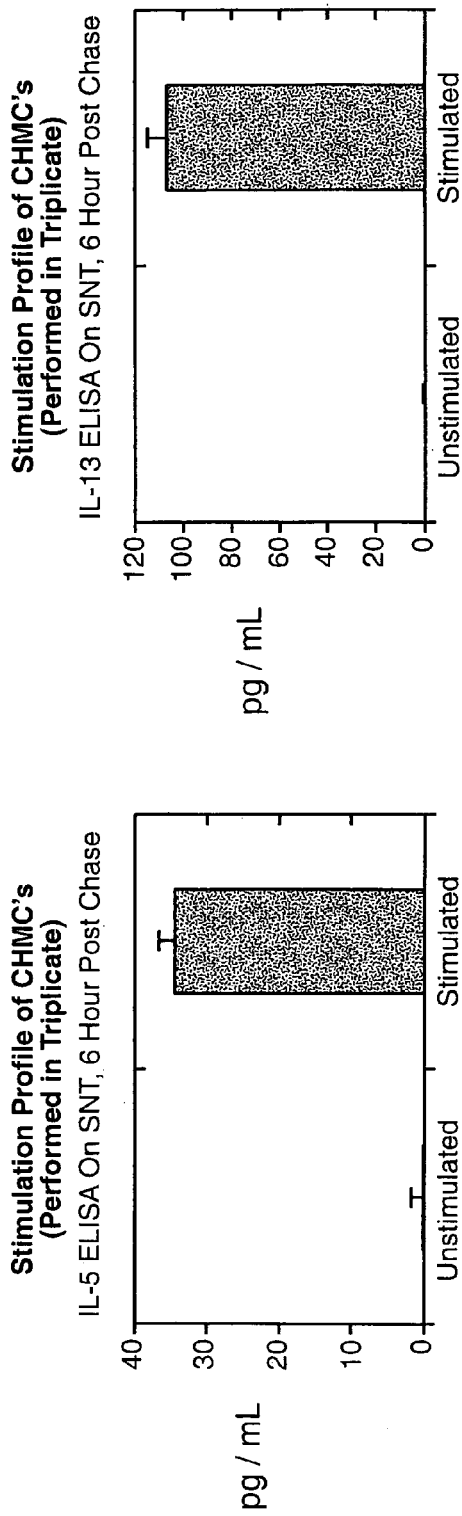
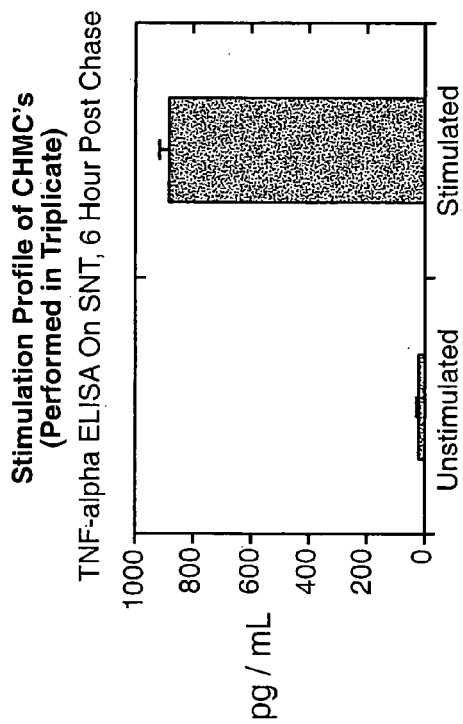
FIG._8F
FIG._8E
FIG._8G

CD Profile Summary For CHMC's

A

CD15, CD11b, and CD13:

| | |
|---|---|
| CD15 pos: | 3% |
| CD11b pos: | 0% |
| CD13 pos: | 35% |
| CD15/13 pos: | 3% |
| CD11b/13 pos: | 2% |
| CD11b/15pos: | 1% |
| | |
| CD15/13 neg: | 55% |
| CD11b/13 neg: | 59% |
| CD11b/15 neg: | 92% |

C

CD15, CD11b, and CD14:

| | |
|---|---|
| CD15 pos: | 4% |
| CD11b pos: | 0% |
| CD14 pos: | 39% |
| CD15/14 pos: | 4% |
| CD11b/14 pos: | 2% |
| CD11b/15pos: | 0% |
| | |
| CD15/14 neg: | 53% |
| CD11b/14 neg: | 56% |
| CD11b/15 neg: | 91% |

B

CD34, CD11b, and CD13:

| | |
|---|---|
| CD34 pos: | 0% |
| CD11b pos: | 0% |
| CD13 pos: | 32% |
| CD34/13 pos: | 1% |
| CD11b/13 pos: | 1% |
| CD11b/15pos: | 0% |
| | |
| CD34/13 neg: | 66% |
| CD11b/13 neg: | 66% |
| CD11b/34 neg: | 97% |

D

CD34, CD11b, and CD14:

| | |
|---|---|
| CD34 pos: | 0% |
| CD11b pos: | 0% |
| CD14 pos: | 37% |
| CD34/14 pos: | 0% |
| CD11b/14 pos: | 2% |
| CD11b/34pos: | 0% |
| | |
| CD34/14 neg: | 58% |
| CD11b/14 neg: | 58% |
| CD11b/34neg: | 96% |

*FIG._9*

PRODUCTION OF CULTURED HUMAN MAST CELLS AND BASOPHILS FOR HIGH THROUGHPUT SMALL MOLECULE DRUG DISCOVERY

This application claims the benefit of U.S. Ser. No. 60/316,723, filed Aug. 31, 2001.

FIELD OF THE INVENTION

The invention relates to methods and compositions for producing a large uniform population of cultured mast cells and basophils cells, and mast and basophil progenitor cell populations, preferably human. The cell populations are suitable for use in high throughput screening methods.

BACKGROUND OF THE INVENTION

At least two types of mast cells are known. These include mast cells of the airway or lung and intestinal mucosa ("mucosal," or $MC_T$), and mast cells of the connective tissue including skin, lymph nodes and intestinal submucosa ($MC_{TC}$). The majority of airway mast cells contain tryptase but lack chymase and carboxypeptidase A. Most connective tissue mast cells, by comparison, contain tryptase, chymase and carboxypeptidase A. Mast cells of different tissues can also be distinguished morphologically. See Bingham, C. O. et al., J. Allergy Clin. Immunol. 105:S527–S534 (February 2000), hereby incorporated by reference.

Mast cell precursors arise from the bone marrow, and enter the circulation as CD34+ mononuclear cells. After migrating to mucosal and submucosal sites in the airway and tissues, mast cell precursors undergo tissue-specific development into mature mast cells. Mature mast cells are characteristically heavily granulated. See Kempuraj, D. et al., Blood 93:3338–46 (May 15, 1999), hereby incorporated by reference.

The granules within mast cells contain preformed inflammatory mediators, including the serine proteases, tryptase and chymase, vasoactive substances such as histamine, and neuroactive agents such as serotonin and nerve growth factor. The rapid release of these preformed mediators is a process known as degranulation, a form of regulated exocytosis, and is generally initiated by an activation event, such as cross-linking of mast cell high-affinity IgE receptors (Fcε receptors), or stimulation by complement components, neuropeptides or other agents. Mast cell activation also leads to the synthesis and release of arachidonic acid metabolites and a variety of de novo synthesized cytokines, including tumor necrosis factor alpha (TNF-alpha), IL-5, and IL-13. See Church, M. and Levi-Schaffer, F., J. Allergy Clin. Immunol. 99:155–60 (February 1997); Bingham, C. O. et al., J. Allergy Clin. Immunol. 105:S527–S534 (February 2000), hereby incorporated by reference.

Mediator release from mast cells plays an important role in immediate and late-phase hypersensitivity, and in inflammation, allergy, parasite infection, and asthma. In the United States alone, over 50 million people suffer from asthma, rhinitis, or some other form of allergy. Therapy for allergy remains limited to blocking the mediators released by mast cells (anti-histamines), non-specific anti-inflammatory agents such as steroids and mast cell stabilizers which are only marginally effective at limiting the symtomatology of allergy. See Perou et al., J. Biol. Chem. 272(47):29790 (1997) and Barbosa et al., Nature 382:262 (1996), both of which are hereby incorporated by reference. Additionally, studies have implicated mast cells in the initiation and severity of neurologic disorders, including multiple sclerosis. See Secor, et al., J. Exp. Med. 191:813–21 (Mar. 6, 2000). Because of their ubiquitous distribution, mast cells are likely to participate in a variety of other conditions, including rheumatoid arthritis, inflammatory bowel disease, and interstitial cystitis. See Church, M. and Levi-Schaffer, F., J. Allergy Clin. Immunol. 99:155–60 (February 1997), hereby incorporated by reference.

Historically, high throughput screening for small molecule agents that effect mast cell activation has been limited by the inability of researchers to reproducibly generate or obtain large enough numbers of a single uniform population of mast cells necessary for conducting large scale screens. It has been very difficult to establish large numbers of these cells in culture due to their terminally differentiated character and the fact that they are frequently localized in specialized deep-tissue microenvironments. As such, purification of mature mast cells from a single donor is labor intensive and typically yields numbers of cells which are far too low for large scale small-molecule drug discovery or for traditional genetic screening.

Several growth factors and cytokines have been shown to be capable of stimulating various phases of mast cell development, maturation and/or activation. Stem cell factor (SCF), also called Steel factor, c-kit ligand, or mast cell growth factor, is known to support mast cell development, survival and function. At least one group has reported generating a population of $10^{15}$ mast cells by treating CD34+ cells with SCF over a period of over 50 weeks. See Kinoshita, et al., Blood 94:496–508 (Jul. 15, 1999), hereby incorporated by reference. The cultures thus established, however, were not homogenous in character, i.e., not exclusively mucosal mast cells. Furthermore, after two months the cells became increasingly tryptase/chymase positive, a phenotype characteristic of connective tissue-type mast cells, rather than mucosal mast cells. These methods also suffered from poor reproducibility by independent groups.

Several groups have reported that IL-6 enhances the SCF-induced development of human mast cells from CD34-positive cells. For example, Saito, et al., reported a slight enhancement of mast cell proliferation after 4–8 weeks of culture with both SCF and IL-6. See, Saito, H. et al., J. Immunol.157:343–50 (1996), hereby incorporated by reference. Kinoshita et al., supra, in contrast, reported that IL-6 inhibited the proliferation of SCF treated mast cells. Still others have reported that the addition of IL-6 to SCF treated mast cells merely promoted their survival. See Yanagida, M., et al. Blood 86:3705–14 (1995), hereby incorporated by reference. In general, reports from these groups indicated that prior methods have produced variable results and have yielded relatively small mast cell populations unsuitable for high throughput screening.

Basophils, like mast cells, arise from bone marrow and are heavily granulated. Basophils synthesize many of the same mediators as mast cells, and express the same high affinity Fcε receptors. Thus, basophils also mediate immediate hypersensitivity reactions to antigen. Additionally, basophils participate in cell-mediated hypersensitivity. Unlike mast cells, basophils mature in the bone marrow, from which they are recruited to tissue sites of inflammation. Basophils and mast cells can be further distinguished based on their surface marker expression patterns.

The tyrosine kinase receptor molecule flt-3 has a general tissue distribution. A ligand for flt-3 has been identified (flt-3 ligand). flt-3 ligand stimulates expansion of hematopoietic progenitor cells in bone marrow and spleen and stimulates mobilization of hematopoietic progenitor cells. See Robinson, et al., J. Hematother. & Stem Cell Res. 9:711–720 (2000).

Zhang et al. have demonstrated a synergistic effect of SCF and flt-3 ligand, when used with other factors, on in vitro expansion of umbilical cord blood cells. See Zhang, X. et al., Chin. J. Biotechnol. 15:189–94 (1999). However, the expanded cells of this report were not characterized phenotypically, and fully differentiated, functional mucosal mast cells were not described.

Accordingly, it is an object of the invention to provide methods of generating large uniform populations of mucosal, airway-type mast cells in vitro. Similarly, the invention also provides methods of generating large uniform populations of connective tissue-type mast cells and basophil cells.

SUMMARY OF THE INVENTION

In accordance with the objects outlined above, the present invention provides methods of producing a proliferated population of CD34-negative cells. The proliferated population of CD34-negative cells can be contacted with one or more cytokines and/or growth factors to produce a proliferated population of mucosal mast cells, a proliferated population of connective tissue-type mast cells, or a proliferated population of basophil cells. The invention also encompasses methods of screening the proliferated populations of the invention, as well as the proliferated populations produced according to the methods described herein.

The method comprises contacting at least one CD34-positive cell with a flt-3 ligand and a stem cell factor to generate a proliferated population of CD34-negative progenitor cells. The proliferated population of CD34-negative progenitors may then be contacted with a stem cell factor and an IL-6 to form a terminally differentiated population of mucosal mast cells. In some aspects, at least one CD34-positive cell is obtained from umbilical cord blood.

In an alternative aspect of the invention, the proliferated population of CD34-negative cells is contacted with an IL-4 and a stem cell factor to form a proliferated population of connective tissue-type mast cells. In yet another aspect, the proliferated population of CD34-negative cells is contacted with an IL-3 and a stem cell factor to form a proliferated population of basophil cells.

In some aspects, the CD34-positive cells used in the methods of the invention are human CD34-positive cells. In preferred embodiments, the cytokines and growth factors used in the described methods are from human. For example, an IL-6 preferably is human IL-6. In addition, an IL-4 used in the methods of the invention preferably is human IL-4. Preferably, an IL-3 used in the methods of the invention is human IL-3. A stem cell factor used as described herein preferably is human stem cell factor. A flt-3 ligand used in the invention preferably is human flt-3 ligand.

The invention also includes methods of screening a proliferated population of mucosal mast cells. The screening methods comprise contacting at least one CD34-positive cell with a flt-3 ligand and a stem cell factor to generate a proliferated population of CD34-negative progenitor cells, contacting the proliferated population of CD34-negative progenitor cells with a stem cell factor and an IL-6 to form a proliferated population of mucosal mast cells, screening the proliferated population of mucosal mast cells with at least one candidate bioactive agent, and evaluating the proliferated population of mucosal mast cells for a mast cell with an altered phenotype. The evaluating may be done, for example, by assaying for tryptase or hexosaminidase, or by a variety of other assays known in the art.

A further aspect of the method comprises adding a library of candidate bioactive agents to the proliferated population of mucosal mast cells. In yet another aspect, the candidate bioactive agent is a small molecule candidate bioactive agent.

Additionally, the invention includes methods of screening a proliferated population of connective tissue-type mast cells. The screening methods comprise contacting at least one CD34-positive cell with a flt-3 ligand and a stem cell factor to generate a proliferated population of CD34-negative progenitor cells, contacting the proliferated population of CD34-negative progenitor cells with a stem cell factor and an IL-4 to form a proliferated population of connective tissue-type mast cells, screening the proliferated population of connective tissue-type mast cells with at least one candidate bioactive agent, and evaluating the proliferated population of connective tissue-type mast cells for a mast cell with an altered phenotype. The evaluating may be done, for example, by assaying for tryptase or hexosaminidase, or by a variety of other assays known in the art.

A further aspect of the method comprises adding a library of candidate bioactive agents to the proliferated population of connective tissue-type mast cells. In yet another aspect, the candidate bioactive agent is a small molecule candidate bioactive agent.

In yet another aspect, the invention includes methods of screening a proliferated population of basophil cells. The screening methods comprise contacting at least one CD34-positive cell with a flt-3 ligand and a stem cell factor to generate a proliferated population of CD34-negative progenitor cells, contacting the proliferated population of CD34-negative progenitor cells with a stem cell factor and an IL-3 to form a proliferated population of basophil cells, screening the proliferated population of basophil cells with at least one candidate bioactive agent, and evaluating the proliferated population of basophil cells for a basophil cell with an altered phenotype. The evaluating may be done by assaying for tryptase or hexosaminidase. The evaluating may be done, for example, by assaying for tryptase or hexosaminidase, or by a variety of other assays known in the art.

The altered phenotype can be decreased degranulation of at least one cell of said proliferated population of mast cells or said proliferated population of basophil cells. The altered phenotype can also be a change in at least one cell's ability to generate leukotrienes or to generate de novo synthesized cytokines. Further aspects of the methods comprise isolating a candidate bioactive agent that causes the altered phenotype.

A further aspect of the method comprises adding a library of candidate bioactive agents to the proliferated population of basophil cells. In yet another aspect, the candidate bioactive agent is a small molecule candidate bioactive agent.

The candidate bioactive agent of the invention can be a peptide. In some aspects, the screening is done by introducing a nucleic acid encoding the peptide to the mast cells or basophil cells of the invention. In some aspects of the invention, the peptide is a random or biased random peptide. The peptide may alternatively be derived from cDNA, from gDNA, or from mRNA.

A flt-3 ligand used in the invention may have the amino acid sequence of SEQ ID NO:1, or fragments or derivatives thereof. A stem cell factor of the invention may have the amino acid sequence of SEQ ID NO:2, or fragments or derivatives thereof. An IL-6 of the methods may have the amino acid sequence of SEQ ID NO:3, or fragments or derivatives thereof. An IL-4 of the methods may have the amino acid sequence of SEQ ID NO:4, or fragments or derivatives thereof. An IL-3 of the methods may have the amino acid sequence of SEQ ID NO:5, or fragments or derivatives thereof.

The proliferated population of cells of the invention may contain $10^8$–$10^{11}$ cells. Therefore, also provided herein is a population of CD34-negative cells which is preferentially the size of at least $10^8$ cells, more preferably at least $10^9$ cells, even more preferably at least $10^{10}$ cells, and most preferably at least $10^{11}$ cells. Also provided herein is a population of mucosal mast cells which is preferentially the size of at least $10^8$ cells, more preferably at least $10^9$ cells, even more preferably at least $10^{10}$ cells, and most preferably at least $10^{11}$ cells. Also provided herein is a population of connective tissue-type mast cells which is preferentially the size of at least $10^8$ cells, more preferably at least $10^9$ cells, even more preferably at least $10^{10}$ cells, and most preferably at least $10^{11}$ cells. Further provided is a population of basophil cells which is preferentially the size of at least $10^8$ cells, more preferably at least $10^9$ cells, even more preferably at least $10^{10}$ cells, and most preferably at least $10^{11}$ cells.

The invention encompasses proliferated cell populations. Thus, a proliferated population of mucosal mast cells, prepared by contacting at least one CD34-positive cell with a flt-3 ligand and a stem cell factor to generate a proliferated population of CD34-negative progenitor cells; and by contacting the proliferated population of CD34-negative progenitor cells with a stem cell factor and an IL-6 to form a proliferated population of mucosal mast cells, is an aspect of the invention.

Additionally, a proliferated population of connective tissue-type mast cells, prepared by contacting at least one CD34-positive cell with a flt-3 ligand and a stem cell factor to generate a proliferated population of CD34-negative progenitor cells; and by contacting the proliferated population of CD34-negative progenitor cells with a stem cell factor and an IL-4 to form a proliferated population of connective tissue-type mast cells, is another aspect the invention.

A proliferated population of basophil cells, prepared by contacting at least one CD34-positive cell with a flt-3 ligand and a stem cell factor to generate a proliferated population of CD34-negative progenitor cells, and by contacting the proliferated population of CD34-negative progenitor cells with a stem cell factor and an IL-3 to form a proliferated population of basophil cells, is a further aspect of the invention. In one embodiment, the basophil cells are positive for the markers CD11b, CD13, and CD25 but are negative for CD14, CD54 and CD117. In a preferred embodiment, the basophils are also characterized by having high affinity IgE receptors.

In a preferred embodiment, the cells of a single population are all derived from or expanded from cells of a single individual.

BRIEF DESCRIPTION OF THE DRAWINGS

FIG. 1 depicts the amino acid sequence of a flt-3 ligand (SEQ ID NO:1).

FIG. 2 depicts the amino acid sequence of a stem cell factor (SEQ ID NO:2).

FIG. 3 depicts the amino acid sequence of an IL-6 (SEQ ID NO:3).

FIG. 4 depicts the amino acid sequence of an IL-4 (SEQ ID NO:4).

FIG. 5 depicts the amino acid sequence of an IL-3 (SEQ ID NO:5).

FIGS. 6A and 6B depict activation of the cultured human mast cells (CHMC's). FIG. 6A shows hexosaminidase enzymatic activity, a traditional measure of mast cell degranulation, following activation with anti-IgE at 1:250, anti-IgE at 1:1000, or 2 µM ionomycin ("Iono"). Activation by anti-IgE represents physiologic activation, and activation by ionomycin represents non-physiological (maximum) activation. FIG. 6B depicts tryptase enzymatic activity, and demonstrates the utility of using tryptase enzyme activity assay to monitor degranulation of the CHMC's of the invention.

FIGS. 7A, 7B, and 7C depict characterization of CHMC's generated from three separate individuals. The separate populations, CHMC.1, CHMC.2 and CHMC.3 were characterized with cell surface markers known to be lineage specific for mast cells (IgE receptor, CD54, CD117) or lineage negative for mast cells (CD11b and CD25), as well as CD13 and CD14, which have variable expression patterns in mast cells.

FIGS. 8A, 8B, 8C, 8D, 8E, 8F and 8G depict degranulation, leukotriene, and cytokine production profiles of CHMC's stimulated via cross-linking the high affinity IgE receptors on CHMC's using rabbit anti-human IgE polyclonal antibody. FIGS. 8A, 8B, and 8C show degranulation as measured by hexosaminidase activity, tryptase activity and histamine release, respectively, in the culture supernatant of unstimulated or stimulated CHMC's (performed in triplicate). FIG. 8D depicts leukotriene-4 (LTC4) generation from unstimulated and stimulated CHMC's. FIGS. 8E–8G depict ELISA results for IL-5, IL-13 and TNF-alpha, respectively, from culture supernatant of unstimulated and stimulated CHMC's. "SNT" refers to supernatant; "Post X-link" means following the crosslinking step with antibody.

FIG. 9, panels A-D, depicts results of cell-surface marker characterization of mucosal CHMC's.

DETAILED DESCRIPTION OF THE INVENTION

The present invention provides methods for producing proliferated populations of CD34-negative progenitor cells, mast cells and basophil cells, suitable for use in screening of candidate agents, such as small molecules, peptides or cDNA fragments, etc. The invention also provides methods of screening the proliferated populations of the inventions. The invention also includes the proliferated cells generated by the described methods.

The invention provides a method for producing a proliferated population of CD34-negative progenitor cells. The method includes contacting at least one CD34-positive cell with a flt-3 ligand and a stem cell factor to generate a proliferated population of CD34-negative progenitor cells. The CD34-negative progenitor cells of the invention are useful in screening or in generating hematopoietic cells, such as mast or basophil cells.

"Progenitor" cells, or "precursor" cells are cells that are capable of differentiation or maturation into a specific terminally differentiated cell type. The CD34-negative progenitors of the invention are cells whose treatment with SCF and flt-3 has mediated their conversion from CD34-positive into CD34-negative cells. Furthermore, the CD34-negative progenitor cells of the invention are capable of differentiation into mucosal mast cells, connective tissue-type mast cells or basophil cells. Thus, in one embodiment, the CD34- negative progenitor cells of the proliferated population are mucosal mast cell progenitors. In another embodiment, the CD34-negative progenitor cells are connective tissue-type progenitor cells. In yet another embodiment, the CD34-negative progenitor cells are basophil progenitor cells.

The methods of the invention comprise contacting at least one CD34-positive cell with a flt-3 ligand and a stem cell factor. "CD34-positive" or "CD34+" cells are cells that express the CD34 surface antigen to which antibodies specific for CD34 will recognize and bind. CD34 is a phenotypic marker of early hematopoietic cells. CD34 is a monomeric type I integral transmembrane glycoprotein of apparent molecular weight of 105 kDA to 120 kDa. The protein is a 373 amino-acid backbone that is heavily glycosylated with up to nine complex-type N-glycans and numerous highly sialylated O-linked glycans. See, e.g., J. Biol. Regul. Homeost. Agents, January–March; 15(1):1–13 (2001); Rev. Clin. Exp.

Hematol. March;5(1):42–61 (2001), both of which are hereby incorporated by reference. Several CD34 monoclonal antibodies for detection of surface expression of CD34 antigen are commercially available.

CD34+ cells may be mammalian CD34+ cells, as described below. Preferably, the CD34+ cells of the invention are rodent CD34+ cells. More preferably, the CD34+ cells are human CD34+ cells.

CD34+ may be obtained from a variety of tissue or blood sources. In one embodiment, the CD34+ are obtained from bone marrow. In a preferred embodiment, the CD34+ are obtained from blood. In a more preferred embodiment, the CD34+ are obtained from umbilical cord blood.

The present invention provides methods for producing a proliferated population of CD34-negative cells comprising contacting at least one CD34-positive (CD34+) cell with a flt-3 ligand. A "flt-3 ligand" is a polypeptide that binds to a flt-3 (also, a "CD135" or "flk2"). Flt-3 is a receptor molecule generally found on progenitor and stem cells, including CD34+ cells.

Full length human flt-3 ligand and those cloned or purified from other mammals contain an extracellular domain, a transmembrane domain and an intracellular domain.

Accordingly, flt-3 ligands may be transmembrane forms of flt-3 ligand. Furthermore, flt-3 ligands may additionally comprise an intracellular domain. In a preferred embodiment, a flt-3 ligand is soluble, and contains amino acid sequence of the full length extracellular domain. Even more preferably, a flt-3 ligand has the sequence of SEQ ID NO:1.

Additionally, a flt-3 ligand may encompass a biologically active fragment of SEQ ID NO:1. "Biologically active" for purposes of the invention means that the flt-3 ligand is capable of binding to a cell expressing flt-3. Additionally, "biologically active" may encompass one or more of the following activities: capable of stimulating cell proliferation in vitro; capable of stimulating expansion and mobilization of progenitor cells in vivo; capable of synergizing with other factors such as CD117 (c-kit) to increase proliferative potential; and capable of activating the immune system by increasing the production of dentritic and natural killer cells in vivo.

A flt-3 ligand may also encompass a biologically active variant of SEQ ID NO:1 or a fragment thereof. A "flt-3 ligand variant" refers to a polypeptide substantially homologous to SEQ ID NO:1 or a fragment thereof. A flt-3 ligand variant may have one or more deletions, insertions or substitutions relative to SEQ ID NO:1 or a fragment thereof. A flt-3 ligand variant is preferably at least 80% identical to a native flt-3 ligand amino acid sequence, even more preferably at least 90% identical. In some cases, the identity is as high as 95–98%.

Determination of percent identity is by standard methods. Variants may be produced by standard methods or may be naturally occurring.

A flt-3 ligand may be obtained from a variety of sources. In one embodiment, a flt-3 ligand is a mammalian flt-3 ligand, as described below. Preferably, a flt-3 ligand is from mouse. More preferably, a flt-3 ligand is from human.

A flt-3 ligand may be provided to one or more CD34+ cells at a range of concentrations. Preferably, a flt-3 ligand is provided at from 5–40 ng/ml. More preferably, a flt-3 ligand is provided at from 10–30 ng/ml. Even more preferably, a flt-3 ligand is provided at 20 ng/ml. Most preferably, the flt-3 ligand of SEQ ID NO:1 is provided at 20 ng/ml.

The present invention provides methods for producing a proliferated population of CD34-negative progenitor cells comprising contacting at least one CD34-positive (CD34+) cell with a flt-3 ligand and a stem cell factor. A "stem cell factor" (also, "SCF," "c-kit ligand," or "Steel factor") is a hematopoietic growth factor or cytokine acting in the early stages of hematopoiesis, and also essential for melanogenesis and fertility. Native SCF is synthesized by the bone marrow stromal cells as either a transmembrane form or a soluble form. SCF is derived from the Steel locus gene, binds as a ligand to the c-kit proto-oncogene product, promotes colony growth of crude hemopoietic cells and supports the development of mast cells. SCF acts at multiple levels of the haemopoietic hierarchy to promote cell survival, proliferation, differentiation, adhesion and functional activation. It is of particular importance in the mast cell and erythroid lineages, but also acts on multipotential stem and progenitor cells, megakaryocytes, and a subset of lymphoid progenitors.

For purposes of the invention, "stem cell factor" refers to both the transmembrane or the soluble form, or to variants or fragments thereof. Preferably, a stem cell factor of the invention has the sequence of SEQ ID NO:2.

Additionally, a stem cell factor may encompass a biologically active fragment of SEQ ID NO:2. "Biologically active" for purposes of the invention means that the stem cell factor is capable of causing CD34+ cells to differentiate into mast cells; alternatively, the stem cell factor is capable of causing proliferated CD34-negative progenitor cells to differentiate into mast cells when combined with IL-6.

A stem cell factor may also encompass a biologically active variant of SEQ ID NO:2 or a fragment thereof. A "stem cell factor variant" refers to a polypeptide substantially homologous to SEQ ID NO:2 or a fragment thereof. A stem cell factor variant may have one or more deletions, insertions or substitutions relative to SEQ ID NO:2 or a fragment thereof. A stem cell factor variant is preferably at least 80% identical to a native stem cell factor amino acid sequence, even more preferably at least 90% identical. In some cases, the identity is as high as 95–98%.

A stem cell factor may be derived from a mammals, as described below, including rodents and humans. Preferably, the stem cell factor of the invention is derived from a rodent. More preferably, the stem cell factor of the invention is human stem cell factor.

A stem cell factor of the invention may be contacted with CD34-positive or CD34-negative progenitor cells at a variety of concentrations. Preferably, a stem cell factor is provided at from 20 ng/ml to 300 ng/ml. More preferably, a stem cell factor of the invention is provided at from 150 ng/ml to 250 ng/ml. Even more preferably, a stem cell factor is provided at 200 ng/ml. Most preferably, the stem cell factor of SEQ ID NO:2 is provided at 200 ng/ml.

The present invention provides a method for producing a proliferated population of CD34-negative progenitor cells comprising contacting at least one CD34-positive (CD34+) cell with a flt-3 ligand and a stem cell factor.

The invention includes methods wherein CD34-positive cells are obtained from umbilical cord blood.

Preferably, the umbilical cord blood is obtained from a single individual. Preferably, the umbilical cord blood is mammalian umbilical cord blood. More preferably, it is rodent umbilical cord blood. Most preferably, the umbilical cord blood of the invention is human umbilical cord blood.

In a preferred embodiment, the proliferated population of CD34-negative progenitor cells are expanded from or derived from cells from a single individual or patient. In one embodiment, the single individual or patient is one with asthma or another pathological condition involving mast cell degranulaton. In another embodiment, the single individual is one with a pathological condition involving basophil degranulation. "Derived from a single individual" means that the cells are proliferated or cultured from a blood or tissue sample taken from a single individual. Preferably a single sample is taken from a single individual. More preferably, a single sample is taken from umbilical cord blood of a single individual.

In other embodiments, the proliferated cell populations of the invention may be expanded from a plurality of individuals.

The proliferated population of CD34-negative progenitor cells is a population of at least $10^6$ cells derived from a single individual; more preferably, the proliferated population contains at least cells derived from a single individual; even more preferably, the proliferated population contains at least $10^8$ cells derived from a single individual. Most preferably, the proliferated population contains at least $10^9$ cells derived from a single individual. In some embodiments, the proliferated population contains at least $10^{10}$ cells derived from a single individual. In still other embodiments, the proliferated population contains at least $10^{11}$ cells derived from a single individual. The desired population size will depend on a variety of factors related to the particular use intended. The desired size may depend, for example, on the type of assay to be performed, the number of cells to be used per candidate agent screened, and the number of candidate agents to be used in a given screen.

The present invention provides a method for producing a proliferated population of mucosal mast cells comprising contacting at least one CD34-positive (CD34+) cell with a flt-3 ligand and a stem cell factor to generate a proliferated population of CD34-negative progenitors; and contacting the proliferated population of CD34-negative progenitors with a stem cell factor and an IL-6 to form a terminally differentiated population of mucosal mast cells.

The method of the invention provides for contacting the proliferated population of CD34-negative progenitors with a stem cell factor and an IL-6 to form a proliferated population of mucosal mast cells. Herein, "mucosal," "mucosal type," "airway," or "airway type" mast cells refers to mast cells that are typical of mast cells obtained from lung. Mucosal mast cells are characterized by specific binding of high affinity IgE and granule release upon cross-linking of IgE receptors with anti-IgE antibody; by having granules containing histamine; by failure to release chymase and by release of tryptase Preferably, the mucosal mast cells of the invention exhibit a tryptase positive/chymase negative phenotype versus a tryptase/chymase positive (connective tissue) phenotype.

The method of the invention provides contacting the proliferated population of CD34-negative progenitor cells with a stem cell factor and IL-4, IL-6, or IL-3. "IL-6' refers to an interleukin-6, which is a cytokine synthesized by mononuclear phagocytes, vascular endothelial cells, fibroblasts and other cells in response to IL-1 and TNF and known to affect B lymphocytes, T lymphocytes and hybrodoma cells. See Abbas, A. K, et al., eds., CELLULAR AND MOLECULAR IMMUNOLOGY, Second Ed., W.B. Saunders Co., Philadelphia, (1994) pp. 250–251.

Accordingly, in a preferred embodiment, an IL-6 of the invention is soluble. Even more preferably, an IL-6 has the sequence of SEQ ID NO:3.

Additionally, an IL-6 may encompass a biologically active fragment of SEQ ID NO:3. "Biologically active" for purposes of the invention means that the IL-6 is capable of enhancing the differentiation of mucosal mast cells from proliferated CD34-negative progenitor cells. "Biologically active" may also include one or more of the following: capable of stimulating formation of osteoclasts; capable of stimulating increased activity of osteoclasts; and capable of acting as a growth factor for tumor cells.

An IL-6 may also encompass a biologically active variant of SEQ ID NO:3 or a fragment thereof. An "IL-6 variant" refers to a polypeptide substantially homologous to SEQ ID NO:3 or a fragment thereof. An IL-6 variant may have one or more deletions, insertions or substitutions relative to SEQ ID NO:3 or a fragment thereof. An IL-6 variant is preferably at least 80% identical to a native IL-6 amino acid sequence, even more preferably at least 90% identical. In some cases, the identity is as high as 95–98%.

An IL-6 may be obtained from a variety of sources. In one embodiment, an IL-6 is a mammalian IL-6, as described below. Preferably, an IL-6 is from a rodent. More preferably, an IL-6 is from human.

An IL-6 may be provided to a proliferated population of CD34-negative progenitor cells at a range of concentrations. Preferably, an IL-6 is provided at from 20–300 ng/ml. More preferably, an IL-6 is provided at from 150–250 ng/ml. Even more preferably, an IL-6 is provided at 200 ng/ml. Most preferably, the IL-6 of SEQ ID NO:3 is provided at 200 ng/ml.

The present invention provides a method for producing a proliferated population of connective tissue-type mast cells comprising contacting at least one CD34-positive (CD34+) cell with a flt-3 ligand and a stem cell factor to generate a proliferated population of CD34-negative progenitors; and contacting the proliferated population of CD34-negative progenitors with a stem cell factor and an IL-4 to form a terminally differentiated population of connective tissue-type mast cells.

The method of the invention provides for contacting the proliferated population of CD34-negative progenitors with a stem cell factor and an IL-4 to form a proliferated population of connective tissue-type mast cells. Herein, "connective tissue type" mast cells or "cutaneous mast cells" refers to mast cells that are typical of mast cells obtained from connective tissues, for example, skin, lymph nodes and intestinal submucosa. Connective tissue-type mast cells are characterized by specific binding of high affinity IgE and granule release upon cross-linking of IgE receptors with anti-IgE antibody; by having granules containing relatively high levels of histamine as compared to mucosal mast cells; and by release of both chymase and tryptase. Preferably, the connective tissue-type mast cells of the invention exhibit a tryptase/chymase positive (connective tissue) phenotype.

In some aspects of the invention, the method provides for contacting the proliferated population of CD34-negative progenitors with a stem cell factor and an IL-4. "IL-4" refers to an interleukin-4, which is a member of the four α-helical cytokine family and an important regulator of allergic reactions.

Accordingly, in a preferred embodiment, an IL-4 of the invention is soluble. Even more preferably, an IL-4 has the sequence of SEQ ID NO:4.

Additionally, an IL-4 may encompass a biologically active fragment of SEQ ID NO:4. "Biologically active" for purposes of the invention means that the IL-4 is capable of enhancing the differentiation of connective tissue-type mast cells from proliferated CD34-negative progenitor cells. "Biologically active" may also include one or more of the following: capable of causing growth and activation of B cells, capable of inhibiting differentiation of Th1 cells and production of interferon-γ, capable of stimulating differentiation of Th2 cells or CD8+ T cells, and/or capable of inhibiting proliferation of natural killer cells.

An IL-4 may also encompass a biologically active variant of SEQ ID NO:4 or a fragment thereof. An "IL-4 variant" refers to a polypeptide substantially homologous to SEQ ID NO:4 or a fragment thereof. An IL-4 variant may have one or more deletions, insertions or substitutions relative to SEQ ID NO:4 or a fragment thereof. An IL-4 variant is preferably at least 80% identical to a native IL-4 amino acid sequence, even more preferably at least 90% identical. In some cases, the identity is as high as 95–98%.

An IL-4 may be obtained from a variety of sources. In one embodiment, an IL-4 is a mammalian IL-4, as described below. Preferably, an IL-4 is from a rodent. More preferably, an IL-4 is from human.

An IL-4 may be provided to a proliferated population of CD34-negative progenitor cells at a range of concentrations. Preferably, an IL-4 is provided at from 20–300 ng/ml. More preferably, an IL-4 is provided at from 150–250 ng/ml. Even more preferably, an IL-4 is provided at 200 ng/ml. Most preferably, the IL-4 of SEQ ID NO:3 is provided at 200 ng/ml.

The present invention provides a method for producing a proliferated population of basophil cells comprising contacting at least one CD34-positive (CD34+) cell with a flt-3 ligand and a stem cell factor to generate a proliferated population of CD34-negative progenitors; and contacting the proliferated population of CD34-negative progenitors with a stem cell factor and an IL-3 to form a terminally differentiated population of connective tissue-type mast cells.

The method of the invention provides for contacting the proliferated population of CD34-negative progenitors with a stem cell factor and an IL-3 to form a proliferated population of basophil cells.

In one aspect of the invention, the method provides for contacting the proliferated population of CD34-negative progenitors with a stem cell factor and an IL-3. "IL-3" refers to an interleukin-3, which is another member of the four α-helical cytokine family. IL-3 is also known as multilineage colony-stimulating factor and is involved in promoting expansion of cells that differentiate into all known mature cell types.

Accordingly, in a preferred embodiment, an IL-3 of the invention is soluble. Even more preferably, an IL-3 has the sequence of SEQ ID NO:5.

Additionally, an IL-3 may encompass a biologically active fragment of SEQ ID NO:3. "Biologically active" for purposes of the invention means that the IL-3 is capable of enhancing the differentiation of basophil cells from proliferated CD34-negative progenitor cells. "Biologically active" may also include the ability to stimulates colony formation of megakaryocytes, neutrophils, or macrophages from bone marrow cultures. For additional activities of IL-3, IL-4, IL-6, and stem cell factor, see Busse, W. W., et al., N. Engl. J. Med. 344:350–62 (February 2001), hereby incorporated by reference.

An IL-3 may also encompass a biologically active variant of SEQ ID NO:5 or a fragment thereof. An "IL-3 variant" refers to a polypeptide substantially homologous to SEQ ID NO:5 or a fragment thereof. An IL-3 variant may have one or more deletions, insertions or substitutions relative to SEQ ID NO:5 or a fragment thereof. An IL-3 variant is preferably at least 80% identical to a native IL-3 amino acid sequence, even more preferably at least 90% identical. In some cases, the identity is as high as 95–98%.

An IL-3 may be obtained from a variety of sources. In one embodiment, an IL-3 is a mammalian IL-3, as described below. Preferably, an IL-3 is from a rodent. More preferably, an IL-3 is from human.

An IL-3 may be provided to a proliferated population of CD34-negative progenitor cells at a range of concentrations. Preferably, an IL-3 is provided at from 20–50 ng/ml. Alternatively, an IL-3 is provided at from 20–40 ng/ml. In yet another embodiment, an IL-3 is provided at 30–50 ng/ml.

"Mature" means that the mast cells or basophil cells of the invention respond in degranulation assays as would cells purified from tissues. "Mature" cells are generally non-dividing, i.e., they are terminally differentiated. "Mature" mucosal mast cells for purposes of the invention, for example, are fully functional mucosal-type mast cells.

"Mature" mast cells and basophils cells possess the ability to become activated. In one embodiment, activated mast cells or basophils are cells that degranulate. In another embodiment, activated mast cells or basophils cells are cells that produce cytokines. In some embodiments, activation is by cross-linking of IgE receptors. In other embodiments, activation is by other physiologic stimulation.

The invention includes methods wherein a proliferated population of CD34-negative progenitor cells is contacted with stem cell factor and an IL-6, an IL-4 or an IL-3. Preferably, the CD34-negative progenitor cells are removed from culture media containing flt-3 ligand and transferred to media containing stem cell factor and the cytokine such that essentially no flt-3 ligand remains in the culture media. In other words, the contacting of CD34-negative progenitor cells with SCF and IL-6, IL-4 or IL-3 is preferably performed with media that is substantially free of flt-3 ligand. Alternatively, the progenitors are contacted with media that is completely free of flt-3 ligand.

As indicated above, the invention includes methods using a flt-3 ligand, a stem cell factor, an IL-6, an IL-4 an IL-3 and a CD34-positive cell or cells, any or all of which may be derived from mammals. Mammalian sources may include rodents (rats, mice, hamsters, guinea pigs, etc.), primates, or farm animals (including sheep, goats, pigs, cows, horses, etc). Mammalian sources may also include buffalo, deer, rabbits, minks, marsupials, or marine mammals including dolphins and whales.

Also included are cells prepared according to the methods of the invention. According to one embodiment, the cells are a proliferated population of mucosal mast cells, prepared by contacting at least one CD34-positive cell with a flt-3 ligand and a stem cell factor to generate a proliferated population of CD34-negative progenitor cells; and by contacting the proliferated population of CD34-negative progenitor cells with a stem cell factor and an IL-6. The resulting population is a proliferated population of mucosal mast cells.

According to another embodiment, the cells are a proliferated population of connective tissue-type mast cells, prepared by contacting at least one CD34-positive cell with a flt-3 ligand and a stem cell factor to generate a proliferated population of CD34-negative progenitor cells; and by contacting the proliferated population of CD34-negative progenitor cells with a stem cell factor and an IL-4. The cells generated as such are a proliferated population of connective tissue-type mast cells.

Hematopoietic cells can be distinguished based on their surface marker expression of CD marker proteins or of various Ig or Ig receptor molecules. For example, mucosal and connective tissue-type mast cells are typically positive for surface expression of high affinity IgE receptors, CD54 and CD117 and negative for surface expression of CD15, CD34, CD25 and CD11b. Both types of mast cells may be positive or negative for the markers CD13 and CD14. Thus, the mucosal mast cells of the invention preferably are CD34-negative cells, and express a high affinity IgE receptor molecule. Preferably, the mucosal mast cells also express a CD54 and a CD117. Preferably, the mucosal mast cells of the invention additionally do not express significant levels of a CD25 or a CD11 b. In some embodiments, the mucosal mast cells of the invention are also negative for expression of CD15 and CD34.

Additionally, the connective tissue-type mast cells of the invention preferably are CD34-negative cells, and express a high affinity IgE receptor molecule. Preferably, the connective tissue-type mast cells also express a CD54 and a CD117. Preferably, the connective tissue-type mast cells of the invention additionally do not express significant levels of a CD25 or a CD11b. In some embodiments, the connective tissue-type mast cells of the invention are also negative for expression of CD15 and CD34.

According to yet another embodiment, the cells are a proliferated population of basophil cells, prepared by contacting at least one CD34-positive cell with a flt-3 ligand and a stem cell factor to generate a proliferated population of CD34-negative progenitor cells; and by contacting the proliferated population of CD34-negative progenitor cells with the stem cell factor and an IL-3. The resulting proliferated population is of basophil cells.

Basophils are characterized by specific binding of high affinity IgE and granule release upon cross-linking of IgE receptors with anti-IgE antibody, and by having granules containing, for example, histamine and heparin. Basophils are typically positive for surface expression of CD11b, CD13 and CD25, but negative for expression of CD14 and CD117. See, for example, Valent, P. et al., Adv. Immunol. 52:335–339 (1992); and Agis, et al., Immunol. 87:535–43 (1996), hereby incorporated by reference. Thus, in one embodiment, the basophils of the invention are CD11b-positive, CD13-positive, and CD25-positive. In a and CD117-negative. The basophils of the invention may also be CD54 positive.

It will be understood by those of skill in the art that the surface marker expression patterns discussed above are not limited to the specific examples provided. For example, basophils isolated from blood may have a slightly different marker expression pattern as compared with basophils developed while in culture. Furthermore, there may be variability in the marker expression patterns for basophils, connective tissue-type mast cells and for mucosal mast cells, depending, for example, on the source of the cells, culture conditions, variability in antibody preparations, etc. Additionally, for mast cell, the specific deep-tissue microenvironment in which they reside affects their surface marker expression pattern. Thus, mast cells's ultimate "fate" (marker character) is determined by the cells around them.

Once made, the compositions of proliferated populations find use in a variety of applications. For example, in a preferred embodiment, the proliferated cells are used in high throughput screening (HTS) methods.

The invention includes methods of screening a population of mucosal mast cells comprising contacting at least one CD34-positive cell with a flt-3 ligand and a stem cell factor to generate a proliferated population of CD34-negative progenitors; contacting the proliferated population of CD34-negative progenitors with a stem cell factor and IL-6 to form a proliferated population of mucosal mast cells; screening the mast cells with at least one candidate bioactive agent; and evaluating the mast cells for a mast cell with an altered phenotype.

The invention also includes methods of screening a population of connective tissue-type mast cells comprising contacting at least one CD34-positive cell with a flt-3 ligand and a stem cell factor to generate a proliferated population of CD34-negative progenitors; contacting the proliferated population of CD34-negative progenitors with a stem cell factor and IL-4 to form a proliferated population of connective tissue-type mast cells; screening the mast cells with at least one candidate bioactive agent; and evaluating the mast cells for a mast cell with an altered phenotype.

The invention further includes methods of screening a population of basophil cells comprising contacting at least one CD34-positive cell with a flt-3 ligand and a stem cell factor to generate a proliferated population of CD34-negative progenitors; contacting the proliferated population of CD34-negative progenitors with a stem cell factor and IL-3 to form a proliferated population of basophil cells; screening the basophil cells with at least one candidate bioactive agent; and evaluating the basophil cells for a basophil cell with an altered phenotype.

In a preferred embodiment, the methods are used to screen candidate bioactive agents for the ability to modulate exocytosis. The candidate bioactive agents may be combined with the cell population before, during or after exocytosis is stimulated, preferably before. In some instances, it may be desirable to determine the effect of the candidate bioactive agent, also referred to as "candidate agents" herein, on the cell wherein exocytosis is not induced or wherein exocytosis is inhibited. The candidate bioactive agent can be added to the cell population exogenously or can be introduced into the cells as described further herein.

The term "candidate bioactive agent" or "exogeneous compound" as used herein describes any molecule, e.g., protein, oligopeptide, small organic molecule, polysaccharide, polynucleotide. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

The invention includes methods as described herein wherein a library of candidate bioactive agents is added to the population of mast cells.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes amino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

The invention includes methods as described herein wherein the candidate bioactive agent is a peptide and the peptide is a random peptide.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114: 1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Left., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an candidate bioactive agent library should be large enough so that at least one of its members will have a structure that gives it affinity for the target. Although it is difficult to gauge the required absolute size of a candidate bioactive agent library, nature provides a hint with the immune response: a diversity of $10^{7-108}$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ to $20^{20}$ different agents. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

The candidate bioactive agents are combined or added to a cell or subpopulation of cells. Suitable cell types for different embodiments are outlined above. By "subpopulation of cells" herein is meant at least two cells, with at least about $10^3$ being preferred, at least about $10^6$ being particularly preferred, and at least about $10^8$ being especially preferred. A single proliferated population of cells of the invention may be divided as appropriate into subpopulations of a desired size for use in a single screen.

The candidate bioactive agent and the proliferated cells are combined. As will be appreciated by those in the art, this may accomplished in any number of ways, including adding the candidate agents to the surface of the cells, to the media containing the cells, or to a surface on which the cells are growing or in contact with; adding the agents into the cells, for example by using vectors that will introduce the agents into the cells (i.e. when the agents are nucleic acids or proteins).

The invention includes methods as described above wherein screening is done by introducing a retroviral vector comprising a nucleic acid encoding said candidate bioactive agent to cells. In some embodiments, the retroviral vector is introduced into the CD34-positive cells. In less preferred embodiments, the retroviral vector is introduced into a proliferated population of the invention.

In a preferred embodiment, the candidate bioactive agents are either nucleic acids or proteins (proteins in this context includes proteins, oligopeptides, and peptides) that are introduced into the proliferated cells using retroviral vectors, as is generally outlined in PCT US97/01019 and PCT US97/01048, both of which are expressly incorporated by reference. Generally, a library of retroviral vectors is made using retroviral packaging cell lines that are helper-defective and are capable of producing all the necessary trans proteins, including gag, pol and env, and RNA molecules that have in cis the ψ packaging signal. Briefly, the library is generated in a retrovirus DNA construct backbone; standard oligonucleotide synthesis is done to generate either the candidate agent or nucleic acid encoding a protein, for example a random peptide, using techniques well known in the art. After generation of the DNA library, the library is cloned into a first primer. The first primer serves as a "cassette", which is inserted into the retroviral construct. The first primer generally contains a number of elements, including for example, the required regulatory sequences (e.g. translation, transcription, promoters, etc), fusion partners, restriction endonuclease (cloning and subcloning) sites, stop codons (preferably in all three frames), regions of complementarity for second strand priming (preferably at the end of the stop codon region as minor deletions or insertions may occur in the random region), etc.

A second primer is then added, which generally consists of some or all of the complementarity region to prime the first primer and optional necessary sequences for a second unique restriction site for subcloning. DNA polymerase is added to make double-stranded oligonucleotides. The double-stranded oligonucleotides are cleaved with the appropriate subcloning restriction endonucleases and subcloned into the target retroviral vectors, described below.

Any number of suitable retroviral vectors may be used. Generally, the retroviral vectors may include: selectable marker genes under the control of internal ribosome entry sites (IRES), which allows for bicistronic operons and thus greatly facilitates the selection of cells expressing peptides at uniformly high levels; and promoters driving expression of a second gene, placed in sense or anti-sense relative to the 5' LTR. Suitable selection genes include, but are not limited to, neomycin, blastocidin, bleomycin, puromycin, and hygromycin resistance genes, as well as self-fluorescent markers such as green fluorescent protein, enzymatic markers such as lacZ, and surface proteins such as CD8, etc.

Preferred vectors include a vector based on the murine stem cell virus (MSCV) (see Hawley et al., Gene Therapy 1:136 (1994)) and a modified MFG virus (Rivere et al., Genetics 92:6733 (1995)), and pBABE, outlined in PCT US97/01019.

The retroviruses may include inducible and constitutive promoters for the expression of the candidate agent (to be distinguished from the IL-4 inducible ε promoter). For example, there are situations wherein it is necessary to induce peptide expression only during certain phases of the selection process. A large number of both inducible and constitutive promoters are known.

In addition, it is possible to configure a retroviral vector to allow inducible expression of retroviral inserts after integration of a single vector in target cells; importantly, the entire system is contained within the single retrovirus. Tet-inducible retroviruses have been designed incorporating the Self-Inactivating (SIN) feature of 3' LTR enhancer/promoter retroviral deletion mutant (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, as defined below, which provide the candidate bioactive agents in a conformationally restricted or stable form; b) targeting sequences, defined below, which allow the localization of the candidate bioactive agent into a subcellular or extracellular compartment; c) rescue sequences as defined below, which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; f) detection sequences, such as labels or reporter molecules or g) any combination of a), b), c), d), e), or f), as well as linker sequences and other proteins as needed.

In a preferred embodiment, the fusion partner is a presentation structure. By "presentation structure" or grammatical equivalents herein is meant a sequence, which, when fused to candidate bioactive agents, causes the candidate agents to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

While the candidate bioactive agents may be either nucleic acid or peptides, presentation structures are preferably used with peptide candidate agents. Thus, synthetic presentation structures, i.e. artificial polypeptides, are capable of presenting a randomized peptide as a conformationally-restricted domain. Generally such presentation structures comprise a first portion joined to the N-terminal end of the randomized peptide, and a second portion joined to the C-terminal end of the peptide; that is, the peptide is inserted into the presentation structure, although variations may be made, as outlined below. To increase the functional isolation of the randomized expression product, the presentation structures are selected or designed to have minimal biologically activity when expressed in the target cell.

Preferred presentation structures maximize accessibility to the peptide by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference). Using this system investigators have isolated peptides capable of high affinity interaction with the appropriate target. In general, coiled-coil structures allow for between 6 to 20 randomized positions.

A preferred coiled-coil presentation structure is as follows: MGCAALESEVSALESEVAS LESEVAALGRGDMPLAAVKS KLSAVKSKLASVKSKLAACGPP (SEQ ID NO:6). The underlined regions represent a coiled-coil leucine zipper region defined previously (see Martin et al., EMBO J. 13(22):5303–5309 (1994), incorporated by reference). The bolded GRGDMP (SEQ ID NO:7) region represents the loop structure and when appropriately replaced with randomized peptides (i.e.candidate bioactive agents, generally depicted herein as (X)n, where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, Kd=10–7, for the proinflammatory cytokine IL-6.

A preferred minibody presentation structure is as follows: MGRNSQATSGFTFSHFYMEWVRGGEYIAASR HKHNKYTTEYSASVKGRYIVSRDTSQSILYLQKKKG-PP (SEQ ID NO:8). The bold, underline regions are the regions which may be randomized. The italized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLSs such as that of the SV40 (monkey virus) large T Antigen (Pro Lys Lys Lys Arg Lys Val (SEQ ID NO:9)), Kalderon (1984), et al., Cell, 39:499–509; the human retinoic acid receptor-β nuclear localization signal (ARRRRP (SEQ ID NO:10)); NFκB p50 (EEVQRKRQKL (SEQ ID NO:11); Ghosh et al., Cell 62:1019 (1990); NFκKB p65 (EEKRKRTYE (SEQ ID NO:12); Nolan et al., Cell 64:961 (1991); and others (see for example Boulikas, J. Cell. Biochem. 55(1):32–58 (1994), hereby incorporated by reference) and double basic NLSs exemplified by that of the *Xenopus* (African clawed toad) protein, nucleoplasmin (Ala Val Lys Arg Pro Ala Ala Thr Lys Lys Ala Gly Gln Ala Lys Lys Lys Lys Leu Asp (SEQ ID NO:13)), Dingwall, et al., Cell, 30:449–458,1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390,1986; Bonnerot, et al., Proc. Natl. Acad. Sci. USA, 84:6795–6799, 1987; Galileo, et al., Proc. Natl. Acad. Sci. USA, 87:458–462,1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound peptide libraries are useful for both the identification of important elements in these processes as well as for the discovery of effective inhibitors. The invention provides methods for presenting the randomized expression product extracellularly or in the cytoplasmic space. For extracellular presentation, a membrane anchoring region is provided at the carboxyl terminus of the peptide presentation structure. The randomized expression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product-containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: 1) class I integral membrane proteins such as IL-2 receptor beta-chain (residues 1–26 are the signal sequence, 241–265 are the transmembrane residues; see Hatakeyama et al., Science 244:551 (1989) and von Heijne et al, Eur. J. Biochem. 174:671 (1988)) and insulin receptor beta chain (residues 1–27 are the signal, 957–959 are the transmembrane domain and 960–1382 are the cytoplasmic domain; see Hatakeyama, supra, and Ebina et al., Cell 40:747 (1985)); 2) class 11 integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8 (MASPLTRFLSLNLLLLGESILGSGEAKPQAP (SEQ ID NO:14); Nakauchi et al., PNAS USA 82:5126 (1985) and 1–21 in the case of ICAM-2 (MSSFGYRTLTVALFTLICCPG (SEQ ID NO:15); Staunton et al., Nature (London) 339:61 (1989)).

These leader sequences deliver the construct to the membrane while the hydrophobic transmembrane domains, placed 3' of the random candidate region, serve to anchor the construct in the membrane. These transmembrane domains are encompassed by amino acids 145–195 from CD8 (PQRPEDCRPRGSVKGTGLDFACDIYIWAPLAGICVALLLSLIITLICYHSR (SEQ ID NO:16); Nakauchi, supra) and 224–256 from ICAM-2 (MVIIVTWSVLLSLFVTSVLLCFIFGQHLRQQR (SEQ ID NO:17); Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT (SEQ ID NO:18), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO:19) (see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the variable region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQDCCGNCSDSEEELPTRL (SEQ ID NO:20), with the bold cysteines being palmitolyated; Stoffel et al., J. Biol. Chem 269:27791 (1994)); from rhodopsin (KQFRNCMLTSLCCGKNPLGD (SEQ ID NO:21); Barnstable et al., J. Mol. Neurosci. 5(3):207 (1994)); and the p21 H-ras I protein (LNPPDESGPGCMSCKCVLS (SEQ ID NO:22); Capon et al., Nature 302:33 (1983)).

In a preferred embodiment, the targeting sequence is a lysozomal targeting sequence, including, for example, a lysosomal degradation sequence such as Lamp-2 (KFERQ (SEQ ID NO:23); Dice, Ann. N.Y. Acad. Sci. 674:58 (1992); or lysosomal membrane sequences from Lamp-1 (MLIP-IAGFFALAGLVLIVLIAYLIGRKRSHAGYQTI (SEQ ID NO:24), Uthayakumar et al., Cell. Mol. Biol. Res. 41:405 (1995)) or Lamp-2 (LVPIAVGAALAGVLILVLLAYFIGLKHHHAGYEQF (SEQ ID NO:25), Konecki et la., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III;
MLRTSSLFTRRVQPSLFSRNILRLQST (SEQ ID NO:26); Schatz, Eur. J. Biochem. 165:1–6 (1987)); mitochondrial inner membrane sequences (yeast cytochrome c oxidase subunit IV;
MLSLRQSIRFFKPATRTLCSSRYLL (SEQ ID NO:27); Schatz, supra); mitochondrial intermembrane space sequences (yeast cytochrome c1;
MFSMLSKRWAQRTLSKSFYSTATGAASKSG KLTQKLVTAGVAAAGITASTLLYADSLTAEAMTA (SEQ ID NO:28); Schatz, supra) or mitochondrial outer membrane sequences (yeast 70 kD outer membrane protein; MKSFITRNKTAILATVMTG-TAIGAYYYYNQLQQQQQRGKK (SEQ ID NO:29); Schatz, supra).

The target sequences may also be endoplasmic reticulum sequences, including the sequences from calreticulin (KDEL (SEQ ID NO:30); Pelham, Royal Society London Transactions B; 1–10 (1992)) or adenovirus E3/19K protein (LYLSRRSFIDEKKMP (SEQ ID NO:31); Jackson et al., EMBO J. 9:3153 (1990).

Furthermore, targeting sequences also include peroxisome sequences (for example, the peroxisome matrix sequence from Luciferase; SKL; Keller et al., PNAS USA 4:3264 (1987)); farnesylation sequences (for example, P21 H-ras 1; LNPPDESGPGCMSCKCVLS (SEQ ID NO:32), with the bold cysteine farnesylated; Capon, supra); geranylgeranylation sequences (for example, protein rab-5A; LTEPTQPTRNQCCSN (SEQ ID NO:33), with the bold cysteines geranylgeranylated; Farnsworth, PNAS USA 91:11963 (1994)); or destruction sequences (cyclin B1; RTALGDIGN (SEQ ID NO:34); Klotzbucher et al., EMBO J. 1:3053 (1996)).

In a preferred embodiment, the targeting sequence is a secretory signal sequence capable of effecting the secretion of the candidate translation product. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398–418. This is particularly useful to generate a peptide capable of binding to the surface of, or affecting the physiology of, a target cell that is other than the host cell, e.g., the cell infected with the retrovirus. In a preferred approach, a fusion product is configured to contain, in series, secretion signal peptide-presentation structure-randomized expression product region-presentation structure. In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS (SEQ ID NO:35); Villinger et al., J. Immunol. 155:3946 (1995)), growth hormone (MATGSRTSLLLAFGLLCLP-WLQEGSAFPT (SEQ ID NO:36); Roskam et al., Nucleic Acids Res. 7:305 (1979)); preproinsulin (MALWMRLL-PLLALLALWGPDPAAAFVN (SEQ ID NO:37); Bell et al., Nature 284:26 (1980)); and influenza HA protein (MKAK-LLVLLYAFVAGDQI (SEQ ID NO:38); Sekikawa et al., PNAS 80:3563)), with cleavage between the non-under-lined-underlined junction. A particularly preferred secretory signal sequence is the signal leader sequence from the secreted cytokine IL-4, which comprises the first 24 amino acids of IL-4 as follows: MGLTSQLLPPLFFLLACAGN-FVHG (SEQ ID NO:39).

In a preferred embodiment, the fusion partner is a rescue sequence. A rescue sequence is a sequence which may be used to purify or isolate either the candidate agent or the nucleic acid encoding it. Thus, for example, peptide rescue sequences include purification sequences such as the His6 tag for use with Ni affinity columns and epitope tags for detection, immunoprecipitation or FACS (fluorescence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the candidate bioactive agent or the nucleic acid encoding it. Thus, for example, peptides may be stabilized by the incorporation of glycines after the initiation methionine (MG or MGG0), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: MG(X)nGGPP (SEQ ID NO:40), where X is any amino acid and n is an integer of at least four.

In one embodiment, the fusion partner is a dimerization sequence. A dimerization sequence allows the non-covalent association of one random peptide to another random peptide, with sufficient affinity to remain associated under normal physiological conditions. This effectively allows small libraries of random peptides (for example, $10^4$) to become large libraries if two peptides per cell are generated which then dimerize, to form an effective library of $10^8$ ($10^4 \times 10^4$). It also allows the formation of longer random peptides, if needed, or more structurally complex random peptide molecules. The dimers may be homo- or heterodimers.

Dimerization sequences may be a single sequence that self-aggregates, or two sequences, each of which is generated in a different retroviral construct. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure.

Suitable dimerization sequences will encompass a wide variety of sequences. Any number of protein-protein interaction sites are known. In addition, dimerization sequences may also be elucidated using standard methods such as the yeast two hybrid system, traditional biochemical affinity binding studies, or even using the present methods.

The fusion partners may be placed anywhere (i.e. N-terminal, C-terminal, internal) in the structure as the biology and activity permits.

In a preferred embodiment, the fusion partner includes a linker or tethering sequence, as generally described in PCT US 97/01019, that can allow the candidate agents to interact with potential targets unhindered. For example, when the candidate bioactive agent is a peptide, useful linkers include glycine-serine polymers (including, for example, (GS)n, (GSGGS)$_n$ (SEQ ID NO:41) and (GGGS)$_n$ (SEQ ID NO:42), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

Preferred embodiments of the invention include candidate bioactive agents linked to fusion partners.

In a preferred embodiment, the fusion partner includes a detection sequence, such as a label or reporter molecule.

The reporter molecule, in one embodiment, may be green fluorescent protein (GFP). The green fluorescent protein from Aequorea Victoria (termed herein "aGFP") is a 238 amino acid protein. The crystal structure of the protein and of several point mutants has been solved (Ormo et al., Science 273, 1392–5, 1996; Yang et al., Nature Biotechnol. 14, 1246–51, 1996). The fluorophore, consisting of a modified tripeptide, is buried inside a relatively rigid beta-can structure, where it is almost completely protected from solvent access. The fluorescence of this protein is sensitive to a number of point mutations (Phillips, G. N., Curr. Opin. Struct. Biol. 7, 821–27, 1997). The fluorescence appears to be a sensitive indication of the preservation of the native structure of the protein, since any disruption of the structure allowing solvent access to the fluorophoric tripeptide will quench the fluorescence.

A GFP from *Renilla mulleri* (termed herein "rGFP"), has been reported recently; see WO 99/49019, hereby expressly incorporated by reference.

A GFP from *Ptilosarcus gurneyi* (termed herein "rGFP"), has been reported recently; see WO 99/49019, hereby expressly incorporated by reference.

Fusions of peptides with GFP are described in detail in U.S. No. 09/169,015, now U.S. Pat. No. 6,180,343; U.S. No. hereby expressly incorporated by reference.

In a preferred embodiment, the candidate bioactive agents are either directly or indirectly labeled. By "labeled" herein is meant that a compound has at least one polypeptide, element, isotope or chemical compound attached to enable the detection of the compound. In general, labels fall into four classes: a) isotopic labels, which may be radioactive or heavy isotopes; b) magnetic, electrical, thermal; c) colored or luminescent dyes; and d) proteins that can be detected or that generate products that can be detected; although labels include enzymes and particles such as magnetic particles as well. Preferred labels include luminescent reporter molecules such as GFP. In a preferred embodiment, the candidate bioactive agent is directly labeled, that is, the agent comprises a label. In an alternate embodiment, the candidate bioactive agent is indirectly labeled. Suitable labels include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, FITC, PE, cy3, cy5 and others described in the 6th Edition of the Molecular Probes Handbook by Richard P. Haugland, hereby expressly incorporated by reference.

The candidate bioactive agents used in the invention include cDNA, gDNA, RNA and random or randomized peptides, as described above. In preferred embodiments, bioactive agents are linked to fusion partners, described above. When the candidate bioactive agents are proteins or peptides, they may be linked to the N-terminus of a protein fusion partner. In some embodiments, peptide or protein agents are linked to the C-terminus of a fusion partner. In other embodiments, peptide or protein agents are linked internally within the structure of a fusion partner, as the biology and activity of the fusion partner permits.

Likewise, when the candidate bioactive agents are cDNA, gDNA or RNA, they may be linked to nucleic acid fusion partners. Nucleic acid candidate bioactive agents may be linked to the 3' end of nucleic acid fusion partners. In some embodiments, nucleic acid agents are linked to the 5' end of nucleic acid fusion partners. In other embodiments, nucleic acid agents are linked internally to a nucleic acid fusion partner.

In addition, the fusion partners, including presentation structures, may be modified, randomized, and/or matured to alter the presentation orientation of the randomized expression product. For example, determinants at the base of the loop may be modified to slightly modify the internal loop peptide tertiary structure, which maintaining the randomized amino acid sequence.

In a preferred embodiment, combinations of fusion partners are used. Thus, for example, any number of combinations of presentation structures, targeting sequences, rescue sequences, and stability sequences may be used, with or without linker sequences.

Thus, candidate agents can include these components, and may then be used to generate a library of fragments, each containing a different random nucleotide sequence that may encode a different peptide. The ligation products are then transformed into bacteria, such as E. coli, and DNA is prepared from the resulting library, as is generally outlined in Kitamura, PNAS USA 92:9146–9150 (1995), hereby expressly incorporated by reference.

Delivery of the library DNA into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T+gag-pol and retrovirus envelope; PA317; and cell lines outlined in Markowitz et al., Virology 167:400 (1988), Markowitz et al., J. Virol. 62:1120 (1988), Li et al., PNAS USA 93:11658 (1996), Kinsella et al., Human Gene Therapy 7:1405 (1996), all of which are incorporated by reference. Preferred systems include PhiNX-eco and PhiNX-ampho or similar cell lines, disclosed in PCT US97/01019.

In general, the candidate agents are added to the cells under reaction conditions that favor agent-target interactions. Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away.

Wherein the candidate agents are nucleic acids, methods known in the art such as calcium phosphate, electroporation, and injection may be used to introduce these to the cells. The exocytic stimulus is generally combined with the cells under physiological conditions. Incubations may be performed at any temperature which facilitates optimal activity, typically between 4 and 40° C. Incubation periods are selected for optimum activity, but may also be optimized to facilitate rapid high through put screening.

A variety of other reagents may be included in the assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for exocytosis detection. Washing or rinsing the cells will be done as will be appreciated by those in the art at different times, and may include the use of filtration, and centrifugation. When second labeling moieties are used, they are preferably added after excess non-bound target molecules are removed, in order to reduce non-specific binding; however, under some circumstances, all the components may be added simultaneously.

In a preferred embodiment, the cells are sorted using fluorescent-activated cell sorting (FACS). In general, KD s of<1 µM are preferred, to allow for retention of binding in the presence of the shear forces present in FACS sorting. In a preferred embodiment, the cells are sorted at very high speeds, for example greater than about 5,000 sorting events per sec, with greater than about 10,000 sorting events per sec being preferred, and greater than about 25,000 sorting events per second being particularly preferred, with speeds of greater than about 50,000 to 100,000 being especially preferred.

Cells processed for stimulation and staining are generally taken up on buffer on ice and filtered prior to cytometry. Cells can be analyzed using a FACSCAN (Becton Dickinson Inc., laser line 488 nm) or a Mo-Flo (Cytomation, Inc., laser lines 350 nM broadband (UV), 488 nm, and 647 nm) Cytometer. Cells are sorted, if desired, using the Mo-Flo.

Wherein the cells are analyzed by microscopy, cells post stimulation or staining are generally mounted onto glass slides and coverslipped; these are directly visualized by brightfield and fluorescence microscopy on an inverted microscope (i.e., TE300, Nikon) using standard BFP, FITC, or TRITC (for example) filter sets. Images can also be obtained using an inverted confocal scanning microscope (Zeiss, Inc., Bio-Rad, Inc.) using standard FITC and TRITC (for example) filter sets.

The sorting results in a subpopulation of cells having the desired exocytic properties. In a preferred embodiment, the parameters are set to identify at least one candidate bioactive agent that modulates exocytosis.

In a preferred embodiment, the bioactive agent is characterized. This will proceed as will be appreciated by those in the art, and generally includes an analysis of the structure, identity, binding affinity and function of the agent. Generally, once identified, the bioactive agent is resynthesized and combined with the target cell to verify the exocytosis modulation under various conditions and in the presence or absence of other various agents. The bioactive can be prepared in a therapeutically effective amount to modulate exocytosis and combined with a suitable pharmaceutical carrier.

In a preferred embodiment, the cell populations or subpopulation can be subjected to various experimental conditions, with and without the candidate agents, and with and without exocytic stimulation or inhibition. Changes in conditions include but are not limited to changes in pH, temperature, buffer or salt concentration, etc. In a preferred embodiment, the pH is changed, generally by increasing or decreasing the pH, usually by from about 0.5 to about 3 pH units. Alternatively, the temperature is altered, with increases or decreases of from about 5° C. to about 30° C. being preferred. Similarly, the salt concentration may be modified, with increases or decreases of from about 0.1 M to about 2 M being preferred.

It is understood by the skilled artisan that the steps of the assays provided herein can vary in order. It is also understood, however, that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additionally washing steps, or segregation, isolation steps. Moreover, it is understood that in some cases detection is in the cells, but can also take place in the media, or vice versa.

The invention also includes use of robotics for performing screening. In a preferred embodiment, the invention includes liquid handling components, including components for loading and unloading fluids at a station or sets of stations. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; holders with cartridges and/or caps; automated lid or cap handlers to remove and replace lids for wells on non-cross contamination plates; tip assemblies for sample distribution with disposable tips; washable tip assemblies for sample distribution; 96 well loading blocks; cooled reagent racks; microtitler plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. The instrument may perform automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of the heat exchangers such as controlled blocks or platforms to provide accurate temperature control of incubating samples from 4° C. to 100° C.; this is in addition to or in place of the station thermocontrollers.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, for example when electronic detection is not done, the instrumentation will include a detector, which can be a wide variety of different detectors, depending on the labels and assay. In a preferred embodiment, useful detectors include a microscope(s) with multiple channels of fluorescence; plate readers to provide fluorescent, ultraviolet and visible spectrophotometric detection with single and dual wavelength endpoint and kinetics capability, fluroescence resonance energy transfer (FRET), luminescence, quenching, two-photon excitation, and intensity redistribution; CCD cameras to capture and transform data and images into quantifiable formats; and a computer workstation.

Robotics instruments can fit in a sterile laminar flow or fume hood, or are enclosed, self-contained systems, for cell culture growth and transformation in multi-well plates or tubes and for hazardous operations. The living cells can be grown under controlled growth conditions, with controls for temperature, humidity, and gas for time series of the live cell assays. Automated transformation of cells and automated colony pickers will facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

The invention also includes methods as described above wherein said candidate bioactive agent is a small molecule candidate bioactive agent.

The invention includes methods as described above wherein said candidate bioactive agent is a peptide and said screening is done by introducing a nucleic acid encoding said peptide to said proliferated cells.

In a preferred embodiment, the invention provides methods for screening a proliferated population of mast cells or basophil cells for at least one cell with an altered phenotype. By "altered," herein is meant any change in a given phenotype.

In one embodiment, the phenotype is the degranulation state of cells of the proliferated population.

Once the cells are made according to the methods herein, one can prime the cells as desired before performing enzymatic, degranulation, or other assays for confirming that the population cell type. Thus, in some embodiments, cell assays of the invention include a priming step. "Priming" involves the use of standard methods for adding IL-4 and IgE to the established cells in culture. These agents are added 3–7 days prior to an activation step. Priming, although not critical to the establishment of the cultures, improves the cells's ability to respond to stimulation. In a preferred embodiment, a screen or assay of the invention includes a step wherein IL-4 and IgE are added to a proliferated cell population, preferably a mast cell, generated using the methods of the invention, prior to an activation step. In other embodiments, no priming step is including in the assays of the invention.

The altered phenotype may be a decrease or an increase in the amount of exocytosis in one cell compared to another cell or in the same cell under different conditions. The measurements can be determined wherein all of the conditions are the same for each measurement, or under various conditions, with or without bioactive agents, or at different stages of the exocytic process. For example, a measurement of exocytosis can be determined in a cell population wherein a candidate bioactive agent is present and wherein the candidate bioactive agent is absent. In another example, the measurements of exocytosis are determined wherein the condition or environment of the populations of cells differ from one another. For example, the cells may be evaluated in the presence or absence of physiological signals, such as exocytic inducers (i.e, $Ca^{++}$, ionomycin, etc.), hormones, antibodies, peptides, antigens, cytokines, growth factors, action potentials, or other cells (i.e. cell-cell contacts). In another example, the measurements of exocytosis are determined at different stages of the exocytic process. In yet another example, the measurements of exocytosis are taken wherein the conditions are the same, and the alterations are between one cell or cell population and another cell or cell population.

Methods of screening comprise evaluating the proliferated cells for an altered phenotype. "Evaluating" includes any method of detecting or determining an alteration in the phenotype of interest. In one embodiment, evaluating encompasses the use of multiparameter FACS assays, as described in U.S. patent application Ser. No. 09/062,330, hereby incorporated by reference.

There are a number of parameters that may be evaluated or assayed to allow the evaluation or detection of alterations in exocytotic pathways, including, but not limited to, light scattering, fluorescent dye uptake, fluorescent dye release, granule exposure, surface granule enzyme activity, and the quantity of granule specific proteins. By assaying or measuring one or more of these parameters, it is possible to detect not only alterations in exocytosis, but alterations of different steps of the exocytotic pathway.

In a preferred embodiment, a candidate bioactive agent is combined with the cells as described herein. In some cases, the candidate bioactive agent can be combined with the cells with an inhibitor of exocytosis or without the pro-exocytic stimulus. Preferably, a pro-exocytic stimulus is added to the cell population which results in a dramatic increase in the fluorescence signal of the dye. The increased cell associated signal is due to coupled endocytosis of the styryl dye and is proportional to the exocytic response in both time and intensity. Conversely, the signal is not increased wherein exocytosis is inhibited or is not induced. Alterations are determined by measuring the fluorescence at either different time points or in different cell populations, and comparing the determinations to one another or to standards. In general, changes of at least about 50% from baseline are preferred, with changes of at least about 75%-100% being more preferred, changes of at least about 250% being particularly preferred, and changes of at least about 1000–2000% being especially preferred. Baseline in this case means the styryl dye uptake of cells prior to exocytic stimulation.

Preferred styryl dyes include, but are not limited to FM1–43, FM4–64, FMI4–68, FM2–10, FM FM1–84, FMI4–27, FM14–29, FM3–25, FM3–14, FM5–55, RH414, FM6FM4–95, FM4–59, FM9–40, and combinations thereof. Preferred dyes such as FM1–43 are only weakly fluorescent in water but very fluorescent when associated with a membrane, such that dye uptake is readily discernable. Suitable dyes are available commercially, i.e., Molecular Probes, Inc., of Eugene, Ore., "Handbook of Fluorescent Probes and Research Chemicals", 6th Edition, 1996, particularly, Chapter 17, and more particularly, Section 2 of Chapter 17, (including referenced related chapter), hereby incorporated herein by reference. Preferably, the dyes are provided in a solution wherein the dye concentration is about 25 to 1000–5000 nM, with from about 50 to about 1000 nM being preferred, and from about 50 to 250 being particularly preferred. The use of styryl dyes is further described in Betz, et al., Current Opinion in Neurobiology, 6:365–371 (1996) also incorporated herein by reference.

Preferably, fluorescent dye uptake is measured in combination with at least one, and preferably two other indicators of exocytosis activity.

In another preferred embodiment, changes in fluorescent dye release are evaluated. The present invention is in part directed to the discovery that low pH concentration dyes, which are normally used to stain lysozomes, also low pH stain exocytic granules. Generally, these dyes can be taken up by the cells passively and concentrate in granules; however, the cells can be induced to take up the dye, i.e., by coupled endocytosis. In a preferred embodiment, a cell population is bathed in a low pH concentration dye such that the dye is taken up by the cells. The cells are preferably washed. The cells can be exposed to a pro-exocytic stimulus and/or inhibitor. In a preferred embodiment, a candidate bioactive agent is combined with the cell population and preferably, the pro-exocytic stimulus. Fluorescence is evaluated. Changes in fluorescent dye release between cells or at different time points in the same cell indicate alterations in exocytosis. Preferably, the alterations are between cells, and most preferably, between cells having different bioactive agents added thereto. Changes of at least about 5% from baseline are preferred, with at least about 25% being more preferred, at least about 50% being particularly preferred and at least about 100% being especially preferred. Baseline in this case means the amount of dye in the cells prior to stimulation.

In this embodiment, low pH concentration dyes are preferred. Such low pH concentration dyes include but are not limited to acridine orange, LYSOTRACKER™ red, LYSOTRACKER™ green, and LYSOTRACKER™ blue. Such dyes are commercially available, i.e., from Molecular Probes, supra, particularly including Chapter 17, Section 4 of Chapter 17, and referenced "related chapters", i.e., Chapter 23. In preferred embodiments, the dyes are administered in a solution wherein the dye is a concentration of about 50 nM to about 25 µM, with from about 5 µM to about 25 µM being preferred, and from about 1 to 5 µM being particularly preferred. The use of low pH concentration dyes is generally described (in regards to lysozome studies) in Haller, et al., Cell Calcium, 19(2):157–165 (1996), hereby incorporated herein by reference.

In an alternative embodiment wherein changes in fluorescent dye release are evaluated, the fluorescence released into the supernatant is evaluated. In this embodiment, either styryl dyes, which reversibly label endocytosed membranes, or low pH concentration dyes are used. In this embodiment, a cell population is bathed in dye such that the dye is taken up into the cells passively or by induction. The cells are then preferably washed. The cells can be exposed to a pro-exocytic stimulus and/or inhibitor, and optionally, a candidate bioactive agent. The cells which are exposed to a pro-exocytic stimulus will release the dye into the extracellular medium. The fluorescence in the medium can be measured or detected. This process is sometimes referred to as destaining the cells. Optionally, an agent for improving and facilitating the detection of the dye in the medium can be added. For example, micelle-forming detergents such as 3-[(3-cholamidopropyl)dimethylammonio]-1-propanesulfonate (CHAPS) increase the fluorescence and thereby allow detection of small amounts of exocytosis activity. Changes in the release of dye will indicate alterations in exocytosis in the same cell, between cells, and most preferably, between cells having different bioactive agents added thereto. In general, changes of at least about 5% from baseline are preferred, with at least about 25% being more preferred, with at least about 50% being particularly preferred and at least about 100% being especially preferred. Baseline in this case means the release of dye prior to exocytotic stimulus. Preferably, dye release when measured in the media is combined with the evaluation of at least one other exocytosis indicator.

In a preferred embodiment, changes in granule exposure are determined. The granules are exposed to the media during exocytosis, i.e., the granules fuse with the cell membrane and expose/release their contents. Therefore, granule exposure is indicative of exocytic activity, and its absence is indicative that exocytosis has not been induced, or has been inhibited. Preferably, granule exposure is detected by a detectable agent which specifically bind to granules. An example of a detectable agent used herein is annexin V, a member of a protein family which displays specific binding to phospholipid (phosphotidylserine) in a divalent ion dependent manner. This protein has been widely used for the measurement of apoptosis (programmed cell death) as cell surface exposure of phosphatidylserine is a hallmark early signal of this process. Surprisingly, it has been determined herein that annexin V specifically binds to exocytic granules when they are exposed at the cell surface during the secretory process; granules internal to the cell are unlabeled. This property of annexin V is used herein to create a single exocytosis assay based on its exocytosis dependent binding. Upon exocytic stimulation of cells, the cells show an increase in annexin binding and fluorescent signal in proportion in both time and intensity to the exocytic response.

In this embodiment, annexin is labelled, either directly or indirectly, and combined with a cell population. Annexin is commercially available, i.e., from PharMingen, San Diego, Calif., or Caltag Laboratories, Millbrae, Calif. Preferably, the annexin is provided in a solution wherein the annexin is in a concentration of about 100 ng/ml to about 500 ng/ml, more preferably, about 500 ng/ml to about 1 µg/ml, and most preferably, from about 1 µg/ml to about 5 µg/ml. In a preferred embodiment, the annexin is directly labelled; for example, annexin may be labelled with a fluorochrome such as fluorecein isothiocyanate (FITC), Alexa dyes, TRITC, AMCA, APC, tricolor, Cy-5, and others known in the art or commercially available. In an alternate preferred embodiment, the annexin is labelled with a first label, such as a hapten such as biotin, and a secondary fluorescent label is used, such as fluorescent streptavidin. Other first and second labelling pairs can be used as will be appreciated by those in the art.

In the preferred embodiment, the cells are subjected to conditions that normally cause exocytosis. Optionally, a candidate bioactive agent is added to the cells. In some cases, it may be desirable to include an inhibitor of exocytosis to determine whether the candidate agent can reverse the inhibition, or to add the candidate bioactive agent without an exocytic stimulus to determine whether the agent induces exocytosis. The cells are preferably washed and fluorescence is detected in the microscope or on the flow-cytometer. Alterations in the detection of annexin binding indicates alterations in exocytosis in the same cell, or between different cells, with or with the same conditions and/or agents combined therewith. In general, changes of at least about 25% from baseline are preferred, with at least about 50% being more preferred, at least about 100 being particularly preferred and at least about 500% being especially preferred. Baseline in this case means the amount of annexin binding prior to exocytic stimulation.

In another preferred embodiment, granule exposure is detected by a cationic dye such as berberine or ruthenium red. Such cationic dyes specifically stain secreting granules. Thus, when exocytosis occurs, and secreting granules are exposed at the cell surface, an increase in fluorescence can be detected. In a preferred embodiment, the cationic dye is combined with a cell population in the presence or absence of an exocytic stimulus and/or inhibitor, and optionally, in the presence or absence of a candidate bioactive agent. In a particularly preferred embodiment, the berberine is combined with a cell and an exocytic stimulus and a candidate bioactive agent to determine whether the candidate bioactive agent can modulate the exocytic activity. Preferably, the cells are washed and then fluorescence is determined. In preferred embodiments, cationic dye evaluation is combined with evaluation of at least one other indicator of exocytosis. The dye is combined with the cells as is known in the art. General methodologies describing berberine are described in Berlin and Enerback, Int. Arch. Allergy Appl. Immunol., 73(3):256–262 (1984) hereby incorporated by reference. In general, changes of at least about 5% from baseline are preferred, with at least about 25% being more preferred, at least about 50% being particularly preferred, and at least about 100% being especially preferred. Baseline in this case means the amount of dye binding prior to stimulation.

Similarly, Con A-FITC can be used, as it binds to the carbohydrate on granule proteins, in a manner similar to those outlined herein.

In another preferred embodiment, changes in surface granule enzyme activity is determined. Secretory granules contain enzymes such as proteases and glycosidases which are released as part of the exocytic process. Frequently, these enzymes are inactive within the granule, due to the low pH, but upon exposure to the extracellular media at physiological pH, they become activated. These enzyme activities can be measured using chromogenic or fluorogenic substrates as components of the extracellular media. This allows detection of exocytic cells in varying approaches.

In one embodiment, sometimes called herein the population based enzyme assay, the generation of signal via cleavage of a chromogenic or fluorogenic substrate can be quantified in the media. That is, the amount of detectable reaction product in the media is related to the amount of enzyme present, and thus to the amount of exocytosis. In this embodiment, it is the media, not the cells, that becomes detectable.

In a preferred embodiment, cells are subjected to an exocytic stimulus, and optionally, a candidate bioactive agent. The chromogenic or fluorogenic substrate is added to the media, and changes in the signal are evaluated, as the enzymes cleave the extracellular substrates.

In an alternate preferred embodiment, sometimes called herein "in situ enzymology assay", fluorogenic substrates that precipitate upon cleavage are used. That is, upon exocytosis a considerable amount of enzyme activity remains cell/granule associated and can be visualized using fluorescent substrates which precipitate at the site of activity. For example, substrates for glucuronidase, such as ELF-97 glucuronide, precipitate on exocytosing cells, but not resting cells, and thus the cells can show increased fluorescence. The fluorescence is a direct measurement of exocytosis and is pH dependent reflecting the pH optima of the exocytosed enzyme. This method also provides a method of distinguishing different subtypes of granules based on their enzyme profile.

In a preferred embodiment, the cell population is subjected to an exocytic stimulus and then incubated with a detectable substrate. A candidate bioactive agent is optionally added. The cells are washed and then viewed in the microscope or flowcytometer.

Preferred granule enzymes include but are not limited to chymase, tryptase, arylsulfatase A, beta-hexosaminidase, beta-glucuronidase, and beta-D-galactosidase. Substrates include ELF-97 glucuronide, N-acetyl beta-D glucoronide, ELF-97 coupled to peptides, etc., many of which are commercially available, i.e., from Molecular Probes, supra, particular Chapter 10, more particularly Section 2 of Chapter 10, and referenced "related chapters".

By detectable substrate is meant that the substrate comprises a fluorescent molecule as further described herein, or can be detected with a fluorescent molecule specific for the substrate or cleaved substrate, i.e., a fluorescent antibody. In a preferred embodiment, the substrate comprises a detectable molecule formed of two fluorescent proteins, i.e., blue and green fluorescent protein (BFP and GFP), and other similar molecules. As is known in the art, constructs of GFP and BFG that hold these two proteins in close proximity allow fluorescence resonance energy transfer (FRET). That is, the excitation spectra of the GFP overlaps the emission spectra of the BFP. Accordingly, exciting the BFP results in GFP emission. If a protease cleavage site is engineered between the GFP and BFP to form a "FRET construct", upon exposure of the FRET construct to an active protease which cleaves the construct, the GFP and BFP molecules separate. Thus, exciting the GFP results in BFP emission and loss of BFP emission.

Preferably, the protease dependent cleavage site inserted between two fluorescent proteins of the FRET construct is specific for a granule specific enzyme. Thus, the FRET construct can be used for detecting granule specific proteases specific for the cleavage site of the FRET construct. In this embodiment, the protease substrate that is combined with the cells or media includes the FRET construct. The FRET system allows for detection of the detectable molecule in its cleaved and uncleaved state, and distinguishes between the two. The system is further described in Xu et al., Nucleic Acid Res. 26(8):2034 (1998); and Miyawaki et al., Nature 388(6645):882–887 (1997) which are incorporated by reference.

The amount of substrate added to the cells or media will depend in part on the enzyme's specific activity and the substrate itself, but generally is about 250 nM to about 1 mM, from about 1 µM to about 100 µM being preferred, and from about 1 µM to about 10 µM being particularly preferred. In general, changes of at least about 5% from baseline are preferred, with at least about 25% being preferred, at least about 100% being particularly preferred and at least about 1000% being especially preferred. Baseline in this case means the amount of substrate cleavage prior to induction of exocytosis.

In a preferred embodiment, changes in the quantity of granule specific proteins are determined. Secretory granules contain proteins which are specifically targeted to the granule compartment due to specific properties of these proteins. Upon exocytic induction, the granule specific proteins are exposed to the surface and detected.

In a preferred embodiment, detectable granule specific proteins are combined with a population of cells and subjected to conditions known to induce exocytosis. Optionally, a bioactive candidate is combined with the cell population and detectable granule specific protein and the granule specific protein is detected. Granule specific proteins include but are not limited to VAMP and synaptotagmin. Also included within the definition of granule specific proteins are the mediators released during exocytosis, including, but not limited to, serotonin, histamine, heparin, hormones, etc.

The quantification of the granule proteins may be done in several ways. In one embodiment, labelled antibodies, (such as fluorescent antibodies), to granule specific proteins are used. In another embodiment, the cells are engineered to contain fusion proteins comprising a granule protein and a detectable molecule. In a preferred embodiment, a detectable molecule is added to the cells for detection. For example, either directly or indirectly labelled antibodies can be used. A preferred embodiment uses a first labelled antibody, with fluorescent labels preferred. Another embodiment uses a first and second label, for example, a labelled secondary antibody. Generally, this embodiment may use any agent that will specifically bind to the granule protein or compound that can be either directly or indirectly labelled.

In a preferred embodiment the labels are engineered into the cells. For example, recombinant proteins are introduced to the cell population which are fusion proteins of a granule specific protein and a detectable molecule. This is generally done by transforming the cells with a fusion nucleic acid encoding a fusion protein comprising a granule specific protein and a detectable molecule. This is generally done as is known in the art, and will depend on the cell type. Generally, for mammalian cells, retroviral vectors and methods are preferred.

The fusion proteins are constructed by methods known in the art. For example, the nucleic acids encoding the granule specific protein is ligated with a nucleic acid encoding a detectable molecule. By detectable molecule herein is meant a molecule that allows a cell or compound comprising the detectable molecule to be distinguished from one that does not contain it, i.e., an epitope, sometimes called an antigen TAG, or a fluorescent molecule. Preferred fluorescent molecules include but are not limited to GFP, BFP, YFP, enzymes including luciferase and β-galactosidase. These constructs can be made in such a way so that upon exocytosis an epitope, internal to the granule, is exposed at the cell surface and can then be detected. The epitope is preferably any detectable peptide which is not generally found on the cytoplasmic membrane, although in some instances, if the epitope is one normally found on the cells, increases may be detected, although this is generally not preferred.

In a preferred embodiment, the cell population containing the fusion protein or detectable granule specific protein is subjected to exocytic conditions. Optionally, a candidate bioactive agent and/or exocytic inhibitor is included. Preferably, the cells are washed. Fluorescence is detected on the cells. In general, changes of at least about 5% from baseline are preferred, with at least about 25% being more preferred, at least about 50% being particularly preferred and at least about 100% being especially preferred. Generally, baseline in this case means amount of fluorescence prior to exocytic stimulus.

In the invention herein, the same characteristic of exocytosis, is evaluated by multiple parameters which results in reduced background and greater specificity. In contrast, FACS has been used in the past to evaluate two different or unrelated characteristics at the same time which identifies cells having those two characteristics, but does not reduce the background for the combined characteristics. The present invention can, however, in addition to the identification of multiple exocytosis properties, be combined with the identification of other cellular characteristics. For example, parameters of general cellular health can be determined and selected for by using i.e., dye Indo-1 indicating a calcium response or calcein blue indicating viability. Other characteristics which are routinely identified by the skilled artisan include but are not limited to: cell size, cell shape, redox state, DNA content, nucleic acid sequence, chromatin structure, RNA content, total protein, antigens, lipids, surface proteins, intracellular receptors, oxidative metabolism, DNA synthesis and degradation and intracellular pH.

In a preferred embodiment, the cells are subjected to conditions that normally cause exocytosis. Pro-exocytic agents include ionomycin, $Ca^{++}$, ionophores (Ionomycin, AZ3187), compound 48/80, substance P, complement C3a/C5a, trypsin, tryptase, insulin, interleukin-3, specific IgE, allergen, anti-IgE, or anti-IgG receptor antibodies. These are provided at concentrations depending on the compound as is known in the art, ranging from 1 picomolar to 10 µM, generally. In some cases, it may be desirable to combine the cells with agents which inhibit exocytosis. Exocytosis inhibitors include but are not limited to Wortmannin, and Genestein, and others known in the art.

The following example(s) serves to more fully describe the manner of using the above-described invention, as well as to set forth the best modes contemplated for carrying out various aspects of the invention. It is understood that the example(s) in no way serves to limit the true scope of this invention, but rather is presented for illustrative purposes. All references cited herein are incorporated by reference.

EXAMPLES

Example 1

Expansion of CD34+ Cells

We expanded a starting population of CD34-positive cells of relatively small size ($1$–$5 \times 10^6$ cells) to a relatively large number of CD34-negative progenitor cells (about $2$–$4 \times 10^9$ cells). The expansion regimen is the most unique aspect of the successful establishment of the subsequent long-term mast cell and basophil cell cultures. What follows is a detailed description of the culture methods employed and reagents used to establish a proliferated population of CD34-negative progenitor cells.

Culture Media:
  Components:
  a) Gibco's STEMPRO-34™ SFM Complete medium:
    STEMPRO-34™-34 SFM, cat. #: 10640, 500 mL
    STEMPRO-34™-34 Nutrient Supplement, cat. #: 10641, 13 mL
  b) L-Glutamine: 200 mM Solution, Mediatech, cat. #: MT 25–005-CI
    add 5 mL per 500 mL STEMPRO-34™
  c) Penicillin/Steptomycin Soln. 100X, HyClone, cat. #: SV30010
    add 5 mL per 500 mL STEMPRO-34™

The method by which the media is made up is critical to the long term health of the culture so an attention to detail is in order when making up the STEMPRO-34™ complete media. The most variable part of the process is the method by which the 13 mL supplement is thawed and mixed prior to addition to the STEMPRO-34™ serum-free basal component. The supplement should be thawed in a 37C. water bath and swirled, not vortexed or shaken, until it is completely in solution. While swirling, take note whether there are any lipids that are not yet in solution. If lipids are present and the component is not uniform in appearance, return to the water bath and repeat the swirling process until the supplement is uniform in appearance. Sometimes this component goes into solution immediately, sometimes after a couple of swirling cycles, and sometimes not at all. If after a couple of hours the component is still not in solution, discard and thaw a fresh unit. Do not ever use the supplement if non-uniform after thaw.

Prepare as follows:
  add 50% of the serum-free STEMPRO-34™ to a filter unit/flask
  pour in the 13 mL supplement rinse the supplement container with approximately 10 mL STEMPRO-34™ and combine with the STEMPRO-34™/supplement combo add the L-glutamine and Pen-Strep bring the total volume up to the appropriate final level filter Cytokines:

a) Recombinant Human Stem Cell Factor, Peprotech, cat. #: 300–07 reconstitute to 100 ug/mL in sterile milliQ water aliquot and store 1 mL aliquots @ −20C.

b) Recombinant Human flt-3-Ligand, Peprotech, cat. #: 300–19 reconstitute to 100 ug/mL in sterile milliQ water aliquot and store 100 uL aliquots @ −20C.

c) Recombinant Human lnterleukin-6, Peprotech, cat. #: 200–06 reconstitute to 100 ug/mL in sterile 100 mM acetic acid aliquot and store 1 mL aliquots @ −20C.

Allcells (Berkeley, Calif.) provided CD34+ isolated from a single donor.

Because there is a degree of variation in the quality and number of CD34+ that Allcells typically provides, the newly delivered cells were transferred to a 15 mL conical tube and brought up to 10 mL in STEMPRO-34™.

A cell count was performed on the viable (phase-bright) cells and the cells were spun at 1200 rpm to pellet. The cells are exceedingly small so it is important to focus in and out as you perform the cell count or you are liable to either miss viable cells or mistake dead cells for viable ones.

The cells were re-suspended to 275 K/mL in 200 ng/mL SCF/20 ng/mL flt-3 ligand in STEMPRO-34™. 20 mL STEMPRO-34™ plus 40 uL SCF and 4 uL flt-3 ligand were added to a 50 mL conical tube. The solution was filter sterilized by passing through a 0.2 um acrodisc filter attached to a 30 mL syringe. It is important to always filter sterilize the media prior to use.

On about day four following the exposure of CD34+ to SCF and flt-3 ligand, the density of the culture was checked by performing a cell count. The culture was diluted to 275 K/mL by adding fresh SCF/flt-3 containing media to the flask.

On about day seven, the culture was transferred to a sterile tube and a cell count was performed. The cells were spun at 1200 rpm and resuspended to 275 K/mL in fresh SCF/flt-3 containing media. The cycle was repeated about two more times by adding fresh media four days after resuspension and resuspending about every seven days later to maximally expand the population.

When the culture was large and being maintained in multiple flasks and the culture was to be resuspended, the contents of all the flasks were combined into a single container prior to performing a cell count. This ensured that an accurate cell count would be achieved and provided for a degree of uniformity of treatment for the entire population. Each flask was checked separately for contamination under the microscope prior to combining them to prevent contamination of the entire population.

Between days 17–24 the culture began to go into decline and failed to expand as rapidly as before ("decline" meaning that dead cells began to appear in the population, i.e., that approximately 5–10% of the total number of cells are dead cells). The cells needed to be monitored on a daily basis during this time because complete failure of the culture can take place in as little as 24 hours. Once the decline had begun, the cells were counted, spun down at 850 rpm for 15 minutes, and resuspended at 350 K/mL to try and squeeze one or two more divisions out of the culture. Again, the cells were monitored daily to avoid failure of the culture.

When greater than 15% cell death was evident and a fair amount of debris was present in the culture, the CD34-negative precursor cells were ready for use.

Example 2

Terminal Differentiation of the Precursor Cells into Mucosal Mast Cells

A second phase can be performed to push the expanded CD34-negative progenitor population towards the desired final product, for example, terminally differentiated mucosal mast cells. Mucosal cultured human mast cells (CHMC's) were derived from CD34+ isolated from umbilical cord blood and treated to form a proliferated population of CD34-negative precursor cells, as above. The 4–5 day add/7th day resuspension cycle for the culture remained essentially the same. except that the culture was seeded at 425 K/mL and 15% additional media was added on about day four or five without performing a cell count. Also, the cytokine composition was modified such that flt-3 ligand was absent and both SCF and IL-6 were added to the complete STEMPRO-34™ media to 200 ng/mL final.

Phase I and II together span approximately 5 weeks. Some death and debris in the culture was evident during weeks 1–3 and there was a phase during weeks 2–5 whereby a small percentage of the culture was no longer be in suspension, but was attached to the surface of the culture vessel.

As during Phase 1, when the culture was to be resuspended on day seven of each cycle, the contents of all flasks were combined into a single container prior to performing a cell count to ensure uniformity of the entire population. Each flask was checked separately for contamination under the microscope prior to combining them to prevent contamination of the entire population.

When the flasks were combined, approximately 75% of the volume was transferred to the communal container, leaving behind about 10 mL or so in the flask. The flask containing the remaining volume was rapped sharply and laterally to dislodge the attached cells. The rapping was repeated at a right angle to the first rap to completely dislodge the cells.

The flask was leaned at a 45 degree angle for a couple of minutes before the remaining volume was transferred to the counting vessel. The cells were spun at 950 rpm for 15 min prior to seeding at 35–50 mL per flask (at 425 K/mL).

Example 3

Terminal Differentiation of the Precursor Cells into Connective Tissue-Type Mast Cells A proliferated population of CD34-negative progenitor cells is prepared as above and treated to form a tryptase/chymase positive (connective tissue) phenotype. The methods are performed as in Example 2 for mucosal mast cells, but with the substitution of IL-4 in place of IL-6. The cells obtained are typical of connective tissue mast cells.

Example 4

Terminal Differentiation of the Precursor Cells into Basophil Cells

Likewise, a proliferated population of CD34-negative precursor cells was prepared in Example 1 above, and used to form a proliferated population of basophil cells. The CD34-negative cells were treated as in Example 2 above, but with the substitution of IL-3 at 20–50 ng/mL in place of IL-6.

I claim:

1. A method of generating cultured mast cells, comprising the steps of:
   (a) contacting at least one CD34-positive cell with a flt-3 ligand and stem cell factor to generate a proliferated population of progenitor cells; and thereafter
   (b) contacting said progenitor cells with said stem cell factor and a cytokine suitable for differentiating the progenitor cells into mast cells, thereby forming a proliferated population of mast cells.

2. The method of claim 1 in which the cytokine is IL-6.

3. The method of claim 2 in which the IL-6 is human IL-6.

4. The method of claim 1 in which the cytokine is IL-4.

5. The method of claim 4 in which the IL-4 is human IL-4.

6. The method of claim 1 in which the flt-3 ligand is human flt-3 ligand.

7. The method of claim 1 in which the stem cell factor is human stem cell factor.

8. The method of claim 1 in which the CD34-positive cell is a human CD34-positive cell.

9. The method of claim 1 in which the CD34-positive cell is obtained from umbilical cord blood.

10. The method of claim 1 in which the proliferated population of progenitor cells comprises at least about $10^8$ cells.

11. The method of claim 1 in which the proliferated population of progenitor cells comprises at least about $10^8$ cells.

12. The method of claim 1 in which the proliferated population of progenitor cells comprises at least about $10^9$ cells.

13. The method of claim 1 in which the proliferated population of progenitor cells comprises at least about $10^{10}$ cells.

14. The method of claim 1 in which the proliferated population of progenitor cells comprises at least about $10^{11}$ cells.

* * * * *

UNITED STATES PATENT AND TRADEMARK OFFICE
CERTIFICATE OF CORRECTION

PATENT NO. : 7,070,996 B2
APPLICATION NO. : 10/053355
DATED : July 4, 2006
INVENTOR(S) : Rossi It is certified that error appears in the above-identified patent and that said Letters Patent is hereby corrected as shown below:

In column 60, line 32, claim 10, "$10^8$" should read --$10^7$--.

Signed and Sealed this

Twenty-first Day of November, 2006

JON W. DUDAS
*Director of the United States Patent and Trademark Office*

SEQUENCE LISTING

<160> NUMBER OF SEQ ID NOS: 42

<210> SEQ ID NO 1
<211> LENGTH: 156
<212> TYPE: PRT
<213> ORGANISM: Homo sapiens

<400> SEQUENCE: 1

```
Met Thr Gln Asp Cys Ser Phe Gln His Ser Pro Ile Ser Ser Asp Phe
1               5                   10                  15

Ala Val Lys Ile Arg Glu Leu Ser Asp Tyr Leu Leu Gln Asp Tyr Pro
            20                  25                  30

Val Thr Val Ala Ser Asn Leu Gln Asp Glu Glu Leu Cys Gly Gly Leu
        35                  40                  45

Trp Arg Leu Val Leu Ala Gln Arg Trp Met Glu Arg Leu Lys Thr Val
50                  55                  60

Ala Gly Ser Lys Met Gln Gly Leu Leu Glu Arg Val Asn Thr Glu Ile
65                  70                  75                  80

His Phe Val Thr Lys Cys Ala Phe Gln Pro Pro Pro Ser Cys Leu Arg
                85                  90                  95

Phe Val Gln Thr Asn Ile Ser Arg Leu Leu Gln Glu Thr Ser Glu Gln
            100                 105                 110

Leu Val Ala Leu Lys Pro Trp Ile Thr Arg Gln Asn Phe Ser Arg Cys
        115                 120                 125

Leu Glu Leu Gln Cys Gln Pro Asp Ser Ser Thr Leu Pro Pro Pro Trp
130                 135                 140

Ser Pro Arg Pro Leu Glu Ala Thr Ala Pro Thr Ala
145                 150                 155
```

<210> SEQ ID NO 2
<211> LENGTH: 165
<212> TYPE: PRT
<213> ORGANISM: Homo sapiens

<400> SEQUENCE: 2

```
Met Glu Gly Ile Cys Arg Asn Arg Val Thr Asn Asn Val Lys Asp Val
1               5                   10                  15

Thr Lys Leu Val Ala Asn Leu Pro Lys Asp Tyr Met Ile Thr Leu Lys
            20                  25                  30

Tyr Val Pro Gly Met Asp Val Leu Pro Ser His Cys Trp Ile Ser Glu
        35                  40                  45

Met Val Val Gln Leu Ser Asp Ser Leu Thr Asp Leu Leu Asp Lys Phe
50                  55                  60

Ser Asn Ile Ser Glu Gly Leu Ser Asn Tyr Ser Ile Ile Asp Lys Leu
65                  70                  75                  80

Val Asn Ile Val Asp Asp Leu Val Glu Cys Val Lys Glu Asn Ser Ser
                85                  90                  95

Lys Asp Leu Lys Lys Ser Phe Lys Ser Pro Glu Pro Arg Leu Phe Thr
            100                 105                 110

Pro Glu Glu Phe Phe Arg Ile Phe Asn Arg Ser Ile Asp Ala Phe Lys
        115                 120                 125

Asp Phe Val Val Ala Ser Glu Thr Ser Asp Cys Val Val Ser Ser Thr
130                 135                 140

Leu Ser Pro Glu Lys Asp Ser Arg Val Ser Val Thr Lys Pro Phe Met
145                 150                 155                 160
```

-continued

Leu Pro Pro Val Ala
              165

<210> SEQ ID NO 3
<211> LENGTH: 184
<212> TYPE: PRT
<213> ORGANISM: Homo sapiens

<400> SEQUENCE: 3

Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Tyr Ile
            20                  25                  30

Leu Asp Gly Ile Ser Ala Leu Arg Lys Glu Thr Cys Asn Lys Ser Asn
        35                  40                  45

Met Cys Glu Ser Ser Lys Glu Ala Leu Ala Glu Asn Asn Leu Asn Leu
    50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
                85                  90                  95

Tyr Leu Glu Tyr Leu Gln Asn Arg Phe Glu Ser Ser Glu Glu Gln Ala
            100                 105                 110

Arg Ala Val Gln Met Ser Thr Lys Val Leu Ile Gln Phe Leu Gln Lys
        115                 120                 125

Lys Ala Lys Asn Leu Asp Ala Ile Thr Thr Pro Asp Pro Thr Thr Asn
    130                 135                 140

Ala Ser Leu Leu Thr Lys Leu Gln Ala Gln Asn Gln Trp Leu Gln Asp
145                 150                 155                 160

Met Thr Thr His Leu Ile Leu Arg Ser Phe Lys Glu Phe Leu Gln Ser
                165                 170                 175

Ser Leu Arg Ala Leu Arg Gln Met
            180

<210> SEQ ID NO 4
<211> LENGTH: 130
<212> TYPE: PRT
<213> ORGANISM: Homo sapiens

<400> SEQUENCE: 4

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser
   130

<210> SEQ ID NO 5
<211> LENGTH: 134
<212> TYPE: PRT
<213> ORGANISM: Homo sapiens

<400> SEQUENCE: 5

Met Ala Pro Met Thr Gln Thr Thr Ser Leu Lys Thr Ser Trp Val Asn
1               5                   10                  15

Cys Ser Asn Met Ile Asp Glu Ile Ile Thr His Leu Lys Gln Pro Pro
            20                  25                  30

Leu Pro Leu Leu Asp Phe Asn Asn Leu Asn Gly Glu Asp Gln Asp Ile
        35                  40                  45

Leu Met Glu Asn Asn Leu Arg Arg Pro Asn Leu Glu Ala Phe Asn Arg
    50                  55                  60

Ala Val Lys Ser Leu Gln Asn Ala Ser Ala Ile Glu Ser Ile Leu Lys
65                  70                  75                  80

Asn Leu Leu Pro Cys Leu Pro Leu Ala Thr Ala Ala Pro Thr Arg His
                85                  90                  95

Pro Ile His Ile Lys Asp Gly Asp Trp Asn Glu Phe Arg Arg Lys Leu
            100                 105                 110

Thr Phe Tyr Leu Lys Thr Leu Glu Asn Ala Gln Ala Gln Gln Thr Thr
        115                 120                 125

Leu Ser Leu Ala Ile Phe
    130

<210> SEQ ID NO 6
<211> LENGTH: 61
<212> TYPE: PRT
<213> ORGANISM: Artificial sequence
<220> FEATURE:
<223> OTHER INFORMATION: coiled-coil presentation structure

<400> SEQUENCE: 6

Met Gly Cys Ala Ala Leu Glu Ser Glu Val Ser Ala Leu Glu Ser Glu
1               5                   10                  15

Val Ala Ser Leu Glu Ser Glu Val Ala Ala Leu Gly Arg Gly Asp Met
            20                  25                  30

Pro Leu Ala Ala Val Lys Ser Lys Leu Ser Ala Val Lys Ser Lys Leu
        35                  40                  45

Ala Ser Val Lys Ser Lys Leu Ala Ala Cys Gly Pro Pro
    50                  55                  60

<210> SEQ ID NO 7
<211> LENGTH: 6
<212> TYPE: PRT
<213> ORGANISM: Artificial sequence
<220> FEATURE:
<223> OTHER INFORMATION: loop structure of coiled-coil presentation
      structure

<400> SEQUENCE: 7

Gly Arg Gly Asp Met Pro
1               5

<210> SEQ ID NO 8
<211> LENGTH: 69
<212> TYPE: PRT

```
<213> ORGANISM: Artificial sequence
<220> FEATURE:
<223> OTHER INFORMATION: minibody presentation structure

<400> SEQUENCE: 8

Met Gly Arg Asn Ser Gln Ala Thr Ser Gly Phe Thr Phe Ser His Phe
1               5                   10                  15

Tyr Met Glu Trp Val Arg Gly Gly Tyr Ile Ala Ala Ser Arg His
        20                  25                  30

Lys His Asn Lys Tyr Thr Thr Glu Tyr Ser Ala Ser Val Lys Gly Arg
            35                  40                  45

Tyr Ile Val Ser Arg Asp Thr Ser Gln Ser Ile Leu Tyr Leu Gln Lys
    50                  55                  60

Lys Lys Gly Pro Pro
65

<210> SEQ ID NO 9
<211> LENGTH: 7
<212> TYPE: PRT
<213> ORGANISM: Simian virus 40

<400> SEQUENCE: 9

Pro Lys Lys Lys Arg Lys Val
1               5

<210> SEQ ID NO 10
<211> LENGTH: 6
<212> TYPE: PRT
<213> ORGANISM: Homo sapiens

<400> SEQUENCE: 10

Ala Arg Arg Arg Arg Pro
1               5

<210> SEQ ID NO 11
<211> LENGTH: 10
<212> TYPE: PRT
<213> ORGANISM: Mus musculus

<400> SEQUENCE: 11

Glu Glu Val Gln Arg Lys Arg Gln Lys Leu
1               5                   10

<210> SEQ ID NO 12
<211> LENGTH: 9
<212> TYPE: PRT
<213> ORGANISM: Mus musculus

<400> SEQUENCE: 12

Glu Glu Lys Arg Lys Arg Thr Tyr Glu
1               5

<210> SEQ ID NO 13
<211> LENGTH: 20
<212> TYPE: PRT
<213> ORGANISM: Xenopus laevis

<400> SEQUENCE: 13

Ala Val Lys Arg Pro Ala Ala Thr Lys Lys Ala Gly Gln Ala Lys Lys
1               5                   10                  15

Lys Lys Leu Asp
            20
```

```
<210> SEQ ID NO 14
<211> LENGTH: 31
<212> TYPE: PRT
<213> ORGANISM: Mus musculus

<400> SEQUENCE: 14

Met Ala Ser Pro Leu Thr Arg Phe Leu Ser Leu Asn Leu Leu Leu Leu
1               5                   10                  15

Gly Glu Ser Ile Leu Gly Ser Gly Glu Ala Lys Pro Gln Ala Pro
            20                  25                  30

<210> SEQ ID NO 15
<211> LENGTH: 21
<212> TYPE: PRT
<213> ORGANISM: Homo sapiens

<400> SEQUENCE: 15

Met Ser Ser Phe Gly Tyr Arg Thr Leu Thr Val Ala Leu Phe Thr Leu
1               5                   10                  15

Ile Cys Cys Pro Gly
            20

<210> SEQ ID NO 16
<211> LENGTH: 51
<212> TYPE: PRT
<213> ORGANISM: Mus musculus

<400> SEQUENCE: 16

Pro Gln Arg Pro Glu Asp Cys Arg Pro Arg Gly Ser Val Lys Gly Thr
1               5                   10                  15

Gly Leu Asp Phe Ala Cys Asp Ile Tyr Ile Trp Ala Pro Leu Ala Gly
            20                  25                  30

Ile Cys Val Ala Leu Leu Leu Ser Leu Ile Ile Thr Leu Ile Cys Tyr
        35                  40                  45

His Ser Arg
    50

<210> SEQ ID NO 17
<211> LENGTH: 33
<212> TYPE: PRT
<213> ORGANISM: Homo sapiens

<400> SEQUENCE: 17

Met Val Ile Ile Val Thr Val Val Ser Val Leu Leu Ser Leu Phe Val
1               5                   10                  15

Thr Ser Val Leu Leu Cys Phe Ile Phe Gly Gln His Leu Arg Gln Gln
            20                  25                  30

Arg

<210> SEQ ID NO 18
<211> LENGTH: 37
<212> TYPE: PRT
<213> ORGANISM: Rattus sp.

<400> SEQUENCE: 18

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30
```

```
Met Gly Leu Leu Thr
         35

<210> SEQ ID NO 19
<211> LENGTH: 14
<212> TYPE: PRT
<213> ORGANISM: Homo sapiens

<400> SEQUENCE: 19

Met Gly Ser Ser Lys Ser Lys Pro Lys Asp Pro Ser Gln Arg
1               5                  10

<210> SEQ ID NO 20
<211> LENGTH: 26
<212> TYPE: PRT
<213> ORGANISM: Homo sapiens

<400> SEQUENCE: 20

Leu Leu Gln Arg Leu Phe Ser Arg Gln Asp Cys Cys Gly Asn Cys Ser
1               5                  10                  15

Asp Ser Glu Glu Glu Leu Pro Thr Arg Leu
            20                  25

<210> SEQ ID NO 21
<211> LENGTH: 20
<212> TYPE: PRT
<213> ORGANISM: Rattus norvegicus

<400> SEQUENCE: 21

Lys Gln Phe Arg Asn Cys Met Leu Thr Ser Leu Cys Cys Gly Lys Asn
1               5                  10                  15

Pro Leu Gly Asp
            20

<210> SEQ ID NO 22
<211> LENGTH: 19
<212> TYPE: PRT
<213> ORGANISM: Homo sapiens

<400> SEQUENCE: 22

Leu Asn Pro Pro Asp Glu Ser Gly Pro Gly Cys Met Ser Cys Lys Cys
1               5                  10                  15

Val Leu Ser

<210> SEQ ID NO 23
<211> LENGTH: 5
<212> TYPE: PRT
<213> ORGANISM: Artificial sequence
<220> FEATURE:
<223> OTHER INFORMATION: lysosomal degradation sequence

<400> SEQUENCE: 23

Lys Phe Glu Arg Gln
1               5

<210> SEQ ID NO 24
<211> LENGTH: 36
<212> TYPE: PRT
<213> ORGANISM: Cricetulus griseus

<400> SEQUENCE: 24

Met Leu Ile Pro Ile Ala Gly Phe Phe Ala Leu Ala Gly Leu Val Leu
1               5                  10                  15
```

```
Ile Val Leu Ile Ala Tyr Leu Ile Gly Arg Lys Arg Ser His Ala Gly
            20                  25                  30

Tyr Gln Thr Ile
        35

<210> SEQ ID NO 25
<211> LENGTH: 35
<212> TYPE: PRT
<213> ORGANISM: Homo sapiens

<400> SEQUENCE: 25

Leu Val Pro Ile Ala Val Gly Ala Ala Leu Ala Gly Val Leu Ile Leu
1               5                   10                  15

Val Leu Leu Ala Tyr Phe Ile Gly Leu Lys His His Ala Gly Tyr
            20                  25                  30

Glu Gln Phe
        35

<210> SEQ ID NO 26
<211> LENGTH: 27
<212> TYPE: PRT
<213> ORGANISM: Saccharomyces cerevisiae

<400> SEQUENCE: 26

Met Leu Arg Thr Ser Ser Leu Phe Thr Arg Arg Val Gln Pro Ser Leu
1               5                   10                  15

Phe Ser Arg Asn Ile Leu Arg Leu Gln Ser Thr
            20                  25

<210> SEQ ID NO 27
<211> LENGTH: 25
<212> TYPE: PRT
<213> ORGANISM: Saccharomyces cerevisiae

<400> SEQUENCE: 27

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 28
<211> LENGTH: 64
<212> TYPE: PRT
<213> ORGANISM: Saccharomyces cerevisiae

<400> SEQUENCE: 28

Met Phe Ser Met Leu Ser Lys Arg Trp Ala Gln Arg Thr Leu Ser Lys
1               5                   10                  15

Ser Phe Tyr Ser Thr Ala Thr Gly Ala Ala Ser Lys Ser Gly Lys Leu
            20                  25                  30

Thr Gln Lys Leu Val Thr Ala Gly Val Ala Ala Ala Gly Ile Thr Ala
        35                  40                  45

Ser Thr Leu Leu Tyr Ala Asp Ser Leu Thr Ala Glu Ala Met Thr Ala
    50                  55                  60

<210> SEQ ID NO 29
<211> LENGTH: 41
<212> TYPE: PRT
<213> ORGANISM: Saccharomyces cerevisiae

<400> SEQUENCE: 29
```

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Tyr Asn Gln Leu
            20                  25                  30

Gln Gln Gln Gln Gln Arg Gly Lys Lys
        35                  40

<210> SEQ ID NO 30
<211> LENGTH: 4
<212> TYPE: PRT
<213> ORGANISM: Homo sapiens

<400> SEQUENCE: 30

Lys Asp Glu Leu
1

<210> SEQ ID NO 31
<211> LENGTH: 15
<212> TYPE: PRT
<213> ORGANISM: unidentified adenovirus

<400> SEQUENCE: 31

Leu Tyr Leu Ser Arg Arg Ser Phe Ile Asp Glu Lys Lys Met Pro
1               5                   10                  15

<210> SEQ ID NO 32
<211> LENGTH: 19
<212> TYPE: PRT
<213> ORGANISM: Homo sapiens

<400> SEQUENCE: 32

Leu Asn Pro Pro Asp Glu Ser Gly Pro Gly Cys Met Ser Cys Lys Cys
1               5                   10                  15

Val Leu Ser

<210> SEQ ID NO 33
<211> LENGTH: 15
<212> TYPE: PRT
<213> ORGANISM: Homo sapiens

<400> SEQUENCE: 33

Leu Thr Glu Pro Thr Gln Pro Thr Arg Asn Gln Cys Cys Ser Asn
1               5                   10                  15

<210> SEQ ID NO 34
<211> LENGTH: 9
<212> TYPE: PRT
<213> ORGANISM: Unknown
<220> FEATURE:
<223> OTHER INFORMATION: cyclin B1 destruction sequence

<400> SEQUENCE: 34

Arg Thr Ala Leu Gly Asp Ile Gly Asn
1               5

<210> SEQ ID NO 35
<211> LENGTH: 20
<212> TYPE: PRT
<213> ORGANISM: Unknown
<220> FEATURE:
<223> OTHER INFORMATION: signal sequence from Interleukin-2

<400> SEQUENCE: 35

```
Met Tyr Arg Met Gln Leu Leu Ser Cys Ile Ala Leu Ser Leu Ala Leu
1               5                   10                  15

Val Thr Asn Ser
            20

<210> SEQ ID NO 36
<211> LENGTH: 29
<212> TYPE: PRT
<213> ORGANISM: Homo sapiens

<400> SEQUENCE: 36

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr
            20                  25

<210> SEQ ID NO 37
<211> LENGTH: 27
<212> TYPE: PRT
<213> ORGANISM: Homo sapiens

<400> SEQUENCE: 37

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn
            20                  25

<210> SEQ ID NO 38
<211> LENGTH: 18
<212> TYPE: PRT
<213> ORGANISM: Influenza virus

<400> SEQUENCE: 38

Met Lys Ala Lys Leu Leu Val Leu Leu Tyr Ala Phe Val Ala Gly Asp
1               5                   10                  15

Gln Ile

<210> SEQ ID NO 39
<211> LENGTH: 24
<212> TYPE: PRT
<213> ORGANISM: Unknown
<220> FEATURE:
<223> OTHER INFORMATION: signal sequence from Interleukin-4

<400> SEQUENCE: 39

Met Gly Leu Thr Ser Gln Leu Leu Pro Pro Leu Phe Phe Leu Leu Ala
1               5                   10                  15

Cys Ala Gly Asn Phe Val His Gly
            20

<210> SEQ ID NO 40
<211> LENGTH: 10
<212> TYPE: PRT
<213> ORGANISM: Artificial sequence
<220> FEATURE:
<223> OTHER INFORMATION: stability sequence
<220> FEATURE:
<221> NAME/KEY: MISC_FEATURE
<222> LOCATION: (3)..(6)
<223> OTHER INFORMATION: "Xaa" at positions 3 to 6 can be any
      amino acid.

<400> SEQUENCE: 40
```

```
Met Gly Xaa Xaa Xaa Xaa Gly Gly Pro Pro
1               5                   10

<210> SEQ ID NO 41
<211> LENGTH: 5
<212> TYPE: PRT
<213> ORGANISM: Artificial sequence
<220> FEATURE:
<223> OTHER INFORMATION: linker consensus sequence

<400> SEQUENCE: 41

Gly Ser Gly Gly Ser
1               5

<210> SEQ ID NO 42
<211> LENGTH: 4
<212> TYPE: PRT
<213> ORGANISM: Artificial sequence
<220> FEATURE:
<223> OTHER INFORMATION: linker consensus sequence

<400> SEQUENCE: 42

Gly Gly Gly Ser
1
```